Figure 1:
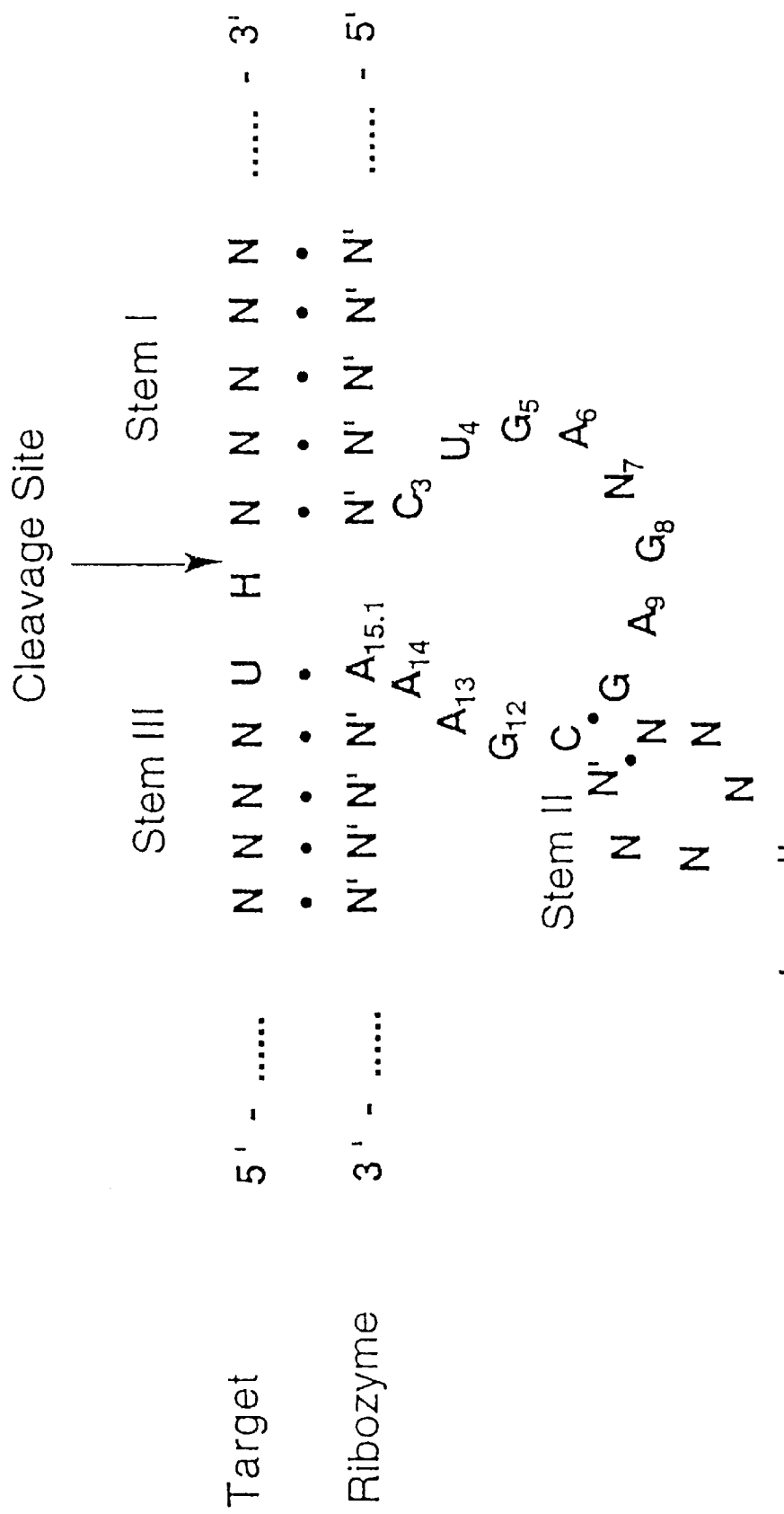

US005877022A

United States Patent [19]
Stinchcomb et al.

[11] Patent Number: 5,877,022
[45] Date of Patent: *Mar. 2, 1999

[54] RIBOZYMES TARGETED TO APO(A) RNA

[75] Inventors: Dan T. Stinchcomb; James McSwiggen, both of Boulder, Colo.; Roger S. Newton; Randy Ramharack, both of Ann Arbor, Mich.

[73] Assignees: Ribozyme Pharmaceuticals, Inc, Boulder, Colo.; Warner Lambert, Ann Arbor, Mich.

[ * ] Notice: The term of this patent shall not extend beyond the expiration date of Pat. Nos. 5,599,706 and 5,658,780.

[21] Appl. No.: 774,310

[22] Filed: Dec. 26, 1996

Related U.S. Application Data

[63] Continuation of Ser. No. 311,760, Sep. 23, 1994, Pat. No. 5,599,706.

[51] Int. Cl.$^6$ .............................. C12Q 1/68; C07H 21/04
[52] U.S. Cl. .......................... 435/375; 435/6; 435/91.31; 435/172.3; 435/320.1; 536/23.1; 536/23.2; 536/24.5
[58] Field of Search .......................... 435/6, 91.31, 320.1, 435/325, 172.3, 366, 37.5; 536/23.1, 23.2, 24.5; 514/44

[56] References Cited

U.S. PATENT DOCUMENTS 4,987,071 1/1991 Cech et al. .

FOREIGN PATENT DOCUMENTS

| 0519463 | 12/1992 | European Pat. Off. . |
|---|---|---|
| 9103162 | 3/1991 | WIPO . |
| 9207065 | 4/1992 | WIPO . |
| 9315187 | 5/1993 | WIPO . |
| 9323569 | 11/1993 | WIPO . |
| 9402595 | 2/1994 | WIPO . |
| 9413688 | 6/1994 | WIPO . |

OTHER PUBLICATIONS

Berg, "A New Serum Type in Man—the LP System," *Acta Pathol. Microbiol. Scand.* 59:369–382 (1963).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chowrira and Burke, "Extenssive Phosphorothioate Substitution Yields Highly Active and Nuclease–Resistant Hairpin Ribozymes," *Nucleic Acids Res.* 20:2835–2840 (1992).

Christofferson et al., "Application of computational technologies to ribozyme biotechnology products," *Journal of Molecular Structure (Theochem)* 311:273–284 (1994).

Collins and Olive, "Reaction Conditions and Kinetics of Self–Cleavage of a Ribozyme Derived From *Neurospora* VS RNA," *Biochemistry* 32:2795–2799 (1993).

Dropulic et al., "Functional Characterization of a U5 Riboyme: Intracellular Suppression of Human Immunodeficiency Virus Type I Expression," *Journal of Virology* 66:1432–1441 (1992).

Elroy–Stein and Moss, "Cytoplasmic Expression System Based on Constitutive Synthesis of Bacteriophage T7 RNA Polymerase in Mammalian Cells," *Proc. Natl. Acad. Sci USA* 87:6743–6747 (1990).

Friedman, "Progress Toward Human Gene Therapy," *Science* 244:1275–1281 (1989).

Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).

Gonzalez–Gronow et al., "Further Characterization of the Cellular Plasminogen Binding Site: Evidence that Plasminogen 2 and Lipoprotein a Complete for the Same Site," *Biochemistry* 28:2374–2377 (1989).

Guerier–Takada et al., "The RNA Moiety of Ribonuclease P Is the Catalytic Subunit of the Enzyme," *Cell* 35:849–85 (1983).

Gurakar et al., "Levels of Lipoprotein Lp(a) Decline with Neomycin and Niacin Treatment," *Atherosclerosis* 57:293–301 (1985).

Hajjar et al., "Lipoportein(a) modulation of endothelial cell surface surface fibrinolysis and its potential role in atherosclerosis," *Nature* 339:303–305 (1989).

Hampel et al., "'Hairpin' Catalytic RNA Model: Evidence for Helices and Sequence Requirement for Substrate RNA," *Nucleic Acids Research* 18:229–304 (1990).

Hampel and Tritz, "RNA Catalytic Properties of the Minimum (–)s TRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

Hertel et al., "Numbering System for the Hammerhead," *Nucleic Acids Res.* 20:3252 (1992).

Jaeger et al., "Improved Predictions of Secondary Structures for RNA," *Proc. Natl. Acad. USA* 86:7706–7710(1989).

Jeffries and Symons, "A Catalytic 13–mer Ribozyme," *Nucleic Acids Research* 17:1371–1377 (1989).

Kashani–Sabet et al., "Reversal of the Malignant Phenotype by an Anti–*ras* Ribozyme," *Antisense Research & Development* 2:3–15 (1992).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lawn et al., "Atherogenesis in transgenic mice expressing human apolipoprotein(a)," *Nature* 360:670–672 (1992).

Leren et al., "Effects of lovastatin alone and in combination with cholestyramine on serum lipids and apolipoproteins in heterozygotes for familial hypercholesterolemia," *Atherosclerosis* 73:135–141 (1988).

(List continued on next page.)

Primary Examiner—John L. LeGuyader
Attorney, Agent, or Firm—Lyon & Lyon LLP

[57] ABSTRACT

Enzymatic RNA molecules which cleave apo(a) mRNA.

20 Claims, 6 Drawing Sheets

OTHER PUBLICATIONS

Lieber et al., "Stable High–Level Gene Expression in Mammalian Cells by T7 Phage RNA Polymerase," *Methods Enzymol.* 217:47–66 (1993).

Lisiewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

McLean et al., "cDNA sequence of human apolipoprotein(a) ishomologous to plasminogen," *Nature* 330:132–137 (1987).

Miles et al., "A potential basis for the thrombotic risks associated with lipoprotein(a)," *Nature* 339:301–303 (1989).

Moliterno et al., "Relation of Plasma Lipoprotein(a) to Infarct Artery Patency in Survivors of Myocardial Infarction," *Circulation* 88:935–940 (1993).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodficiency Virus Type 1 Expression by a Hairpin Ribozyme," *Proc. Natl. Acad. Sci. USA* 89:10802–10806 (1992).

Perreault et al., "Relationship between 2'–Hydroxyls and Magnesium Binding in the Hammerhead RNA Domain: A Model for Ribozyme Catalysis," *Biochemistry* 30:4020–4025 (199.

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Roemer and Friedman, "Concepts and strategies for human gene therapy," *Eur. J. Biochem.* 208:211–225 (1992).

Rossi et al., "Ribozymes as Anti–HIV–1 Therapeutic Agents: Principles, Applications, and Problems," *Aids Research and Human Retroviruses* 8:183–189 (1992).

Rubino et al., "Nucleotide sequence and structural analysis of two satellite RNA associated with chicory yellow mottle virus," *J. General Virology* 71:1897–1903 (1990).

Sarver et al., "Catalytic RNAs (Ribozymes): A New Frontier in Biomedical Applications," *AIDS Res. Revs.* 2:259–285 (1992).

Saville and Collins, "A Site–Specific Self–Cleavage Reaction Performed by a Novel RNA In Neurospora Mitochondria," *Cell* 61:685–696 (1990).

Saville and Collins, "RNA–Mediated Ligation of Self–Cleavage Products of a *Neurospora* Mitochondrial Plasmid Transcript," *Proc. Natl. Acad. USA* 77:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scanu et al., "Lipoprotein(a) and Atherosclerosis," *Annals of Internal Medicine* 115:209–218 (1991).

Scaringe et al., "Chemical synthesis of biologically active oligoribonucleotides using β–cyanoethyl protected ribonucleotide phosphoramisdites," *Nucl Acids Res.* 18:5433–5441 (1990).

Scott, "Lipoprotein(a): Thrombotic and atherogenic," *BMJ* 303:663–664 (1991).

Stull and Szoka, "Antigene, Ribozyme and Aptamer Nucleic Acid Drugs: Progress and Prospects," *Pharmaceutical Research* 12:465–483 (1995).

Symons, "Ribozymes," *Current Opinion in Structural Biology* 4(3):322–330 (1994).

Taira et al., "Construction of a novel RNA–transcript–trimming plasmid which can be used both in vitro in place of run–off and (G)–free transcriptions anad in vivo as multi–sequences transcription vectors," *Nuclei Acids Research* 19:5125–5130 (1991).

*Textbook of Medical Physiology*, Guton, A.C., Saunders Company, Philadelphia pp. 761–764 (1991).

Tomlinson et al.m "Rhesus Monkey Apolipoprotein(a)," *J. Biol. Chem.* 264:5957–5965 (1989).

Uhlenbeck, "A Small Catalytic Oligoribonucleotide," *Nature* 328:596–600 (1987).

Usman et al., "Automated Chemical Synthesis of Long Oligoribonucleotides Using 2'–O–Silylated Ribonucleotide 3'–O–Phosphoramidites on a Controlled–Pore Glass Support: Synthesis of a 43–Nucleotide Sequence Similar to the 3'–Half Molecule of an *Escherichis coli* Formylmethoionine tRNA," *J. Am. Chem. Soc.* 109:7845–7854 (1987).

Usman and Cedergren, "Exploiting the chemical synthesis of RNA," *TIBS* 17:334–339 (1992).

Utermann "The Mysteries of Lipoprotein(a)," *Science* 246:904–910(1989).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing and HIV–1 RNA–Specific Ribozyme," *Journal of Virology* 65:5531–5534 (1994).

Williams et al., "Occlusive Arterial Thrombosis in Cynomolgus Monkeys with Varying Plasma Concentrations of Lipoprotein(a)," *Arteriosclerosis and Thrombosis* 13:548–554 (1993).

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zhou et al., "Synthesis of Functional mRNA in Mammalian Cells by Bacteriophage T3 RNA Polymerase," *Mol. Cell. Biol.* 10:4529–4537 (1990).

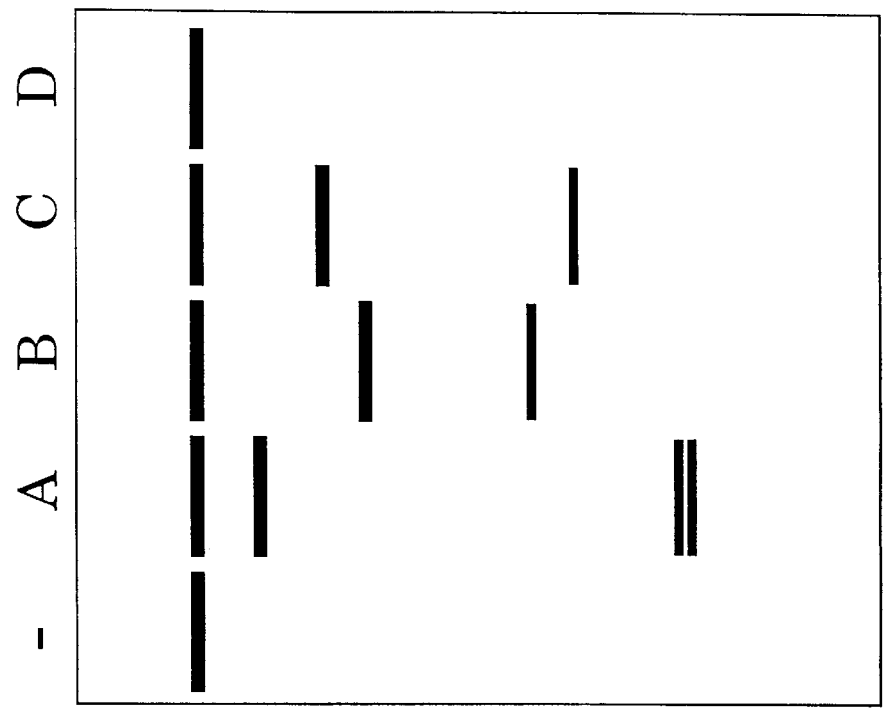
FIG. 6.
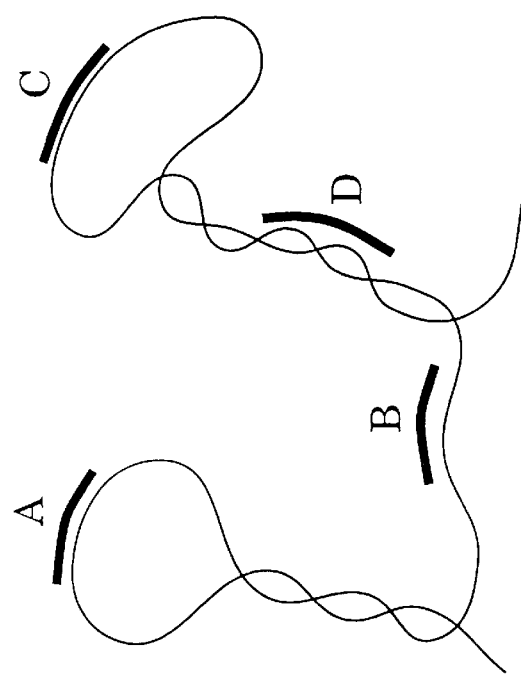
- Body-labeled transcript (not purified)
- DNA oligo (10 nM, 100 nM and 1000 nM)
- RNAse H (0.08 - 1.0 u/μl)
- 37°C, 10 min

SEQUENCE LISTING ( 1 ) GENERAL INFORMATION:

( i i i ) NUMBER OF SEQUENCES: 392

( 2 ) INFORMATION FOR SEQ ID NO:1:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for any
        base. The letter "H"stands for
        A, U, or C.

( x i ) SEQUENCE DESCRIPTION: SEQ ID NO:1:

N N N N U H N N N N   N       1 1

( 2 ) INFORMATION FOR SEQ ID NO:2:

( i ) SEQUENCE CHARACTERISTICS:
      ( A ) LENGTH: 28 base pairs
      ( B ) TYPE: nucleic acid
      ( C ) STRANDEDNESS: single (D) TOPOLOGY: linear (ix) FEATURE:
(D) OTHER INFORMATION: The letter "N"stands for any base.

(xi) SEQUENCE DESCRIPTION: SEQ ID NO:2:

NNNNNCUGAN GAGNNNNNNC GAAANNNN 28

(2) INFORMATION FOR SEQ ID NO:3:

(i) SEQUENCE CHARACTERISTICS:
(A) LENGTH: 14 base pairs
(B) TYPE: nucleic acid
(C) STRANDEDNESS: single
(D) TOPOLOGY: linear (ix) FEATURE:
(D) OTHER INFORMATION: The letter "N"stands for any base. The leter "Y"stands for U or C. The letter "H"stands for A, U, or C.

(xi) SEQUENCE DESCRIPTION: SEQ ID NO:3:

NNNYNGHYNN NNNN 14

(2) INFORMATION FOR SEQ ID NO:4:

(i) SEQUENCE CHARACTERISTICS:
(A) LENGTH: 50 base pairs
(B) TYPE: nucleic acid
(C) STRANDEDNESS: single
(D) TOPOLOGY: linear (ix) FEATURE:
(D) OTHER INFORMATION: The letter "N"stands for any base.

(xi) SEQUENCE DESCRIPTION: SEQ ID NO:4:

NNNNNNGAA GNNNNNNNN NAAACANNNN NNNNNNACA UUACNNNNN 50

(2) INFORMATION FOR SEQ ID NO:5:

(i) SEQUENCE CHARACTERISTICS:
(A) LENGTH: 85 base pairs
(B) TYPE: nucleic acid
(C) STRANDEDNESS: single
(D) TOPOLOGY: linear (xi) SEQUENCE DESCRIPTION: SEQ ID NO:5:

UGGCCGGCAU GGUCCCAGCC UCCUCGCUGG CGCCGGCUGG GCAACAUUCC GAGGGGACCG 60

UCCCCUCGGU AAUGGCGAAU GGGAC 85

(2) INFORMATION FOR SEQ ID NO:6:

(i) SEQUENCE CHARACTERISTICS:
(A) LENGTH: 176 base pairs
(B) TYPE: nucleic acid
(C) STRANDEDNESS: single
(D) TOPOLOGY: linear (xi) SEQUENCE DESCRIPTION: SEQ ID NO:6:

GGGAAAGCUU GCGAAGGGCG UCGUCGCCCC GAGCGGUAGU AAGCAGGGAA CUCACCUCCA 60

AUUUCAGUAC UGAAAUUGUC GUAGCAGUUG ACUACUGUUA UGUGAUUGGU AGAGGCUAAG 120

UGACGGUAUU GGCGUAAGUC AGUAUUGCAG CACAGCACAA GCCCGCUUGC GAGAAU 176

(2) INFORMATION FOR SEQ ID NO:7:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

CCAGGAUUGC UACCA 15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

ACAGAGUUAU CGAGG 15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GAGUUAUCGA GGCAC 15

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCAAGCUUGG UCAUC 15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CAAUGCUCAG ACGCA 15

( 2 ) INFORMATION FOR SEQ ID NO:12:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GACUGUUACC CCGGU 15

( 2 ) INFORMATION FOR SEQ ID NO:13:

( i ) SEQUENCE CHARACTERISTICS:
        ( A ) LENGTH: 15 base pairs ( B ) TYPE: nucleic acid
( C ) STRANDEDNESS: single
( D ) TOPOLOGY: linear ( x i ) SEQUENCE DESCRIPTION: SEQ ID NO:13:

CCCCGGUUCC AAGCC 15

( 2 ) INFORMATION FOR SEQ ID NO:14:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:14:

CCCGGUUCCA AGCCU 15

( 2 ) INFORMATION FOR SEQ ID NO:15:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:15:

CAAGCCUAGA GGCUC 15

( 2 ) INFORMATION FOR SEQ ID NO:16:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:16:

CCAUGGUAAU GGACA 15

( 2 ) INFORMATION FOR SEQ ID NO:17:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:17:

GCAUAGUCGG ACCCC 15

( 2 ) INFORMATION FOR SEQ ID NO:18:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:18:

CCACGGUAAU GGACA 15

( 2 ) INFORMATION FOR SEQ ID NO:19:

( i ) SEQUENCE CHARACTERISTICS:
( A ) LENGTH: 15 base pairs
( B ) TYPE: nucleic acid
( C ) STRANDEDNESS: single (D) TOPOLOGY: linear (xi) SEQUENCE DESCRIPTION: SEQ ID NO:19:

UCCAGAUCCU GUGGC 15

(2) INFORMATION FOR SEQ ID NO:20:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:20:

AGCCCCUUAU UGUUA 15

(2) INFORMATION FOR SEQ ID NO:21:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:21:

GCCCCUUAUU GUUAU 15

(2) INFORMATION FOR SEQ ID NO:22:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:22:

CCCUUAUUGU UAUAC 15

(2) INFORMATION FOR SEQ ID NO:23:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:23:

GGCUCCUUCU GAACA 15

(2) INFORMATION FOR SEQ ID NO:24:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:24:

GCUCCUUCUG AACAA 15

(2) INFORMATION FOR SEQ ID NO:25:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:25:

AAGAACUACU GCCGA                                                                15

( 2 ) INFORMATION FOR SEQ ID NO:26:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:26:

CCGAAAUCCA GAUCC                                                                15

( 2 ) INFORMATION FOR SEQ ID NO:27:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:27:

AGCCCCUUGG UGUUA                                                                15

( 2 ) INFORMATION FOR SEQ ID NO:28:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

UUGGUGUUAU ACAAC                                                                15

( 2 ) INFORMATION FOR SEQ ID NO:29:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

CGAUGCUCAG AUGCA                                                                15

( 2 ) INFORMATION FOR SEQ ID NO:30:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

CAAGCCUAGA GGCUU                                                                15

( 2 ) INFORMATION FOR SEQ ID NO:31:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

GGCUUUUUUU GAACA                                                                                       15

( 2 ) INFORMATION FOR SEQ ID NO:32:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

UGCUACUACC AUUAU                                                                                       15

( 2 ) INFORMATION FOR SEQ ID NO:33:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

CUACCAUUAU GGACA                                                                                       15

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

UACCAUUAUG GACAG                                                                                       15

( 2 ) INFORMATION FOR SEQ ID NO:35:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

AAGAACUUGC CAAGC                                                                                       15

( 2 ) INFORMATION FOR SEQ ID NO:36:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

CCAGCAUAGU CGGAC                                                                                       15

( 2 ) INFORMATION FOR SEQ ID NO:37:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

CUGAGAUUCG CCCUU                                                                                       15

( 2 ) INFORMATION FOR SEQ ID NO:38:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:38:

UGAGAUUCGC CCUUG 15

( 2 ) INFORMATION FOR SEQ ID NO:39:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:39:

UCGCCCUUGG UGUUA 15

( 2 ) INFORMATION FOR SEQ ID NO:40:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:40:

CAUGGAUCCC AGUGU 15

( 2 ) INFORMATION FOR SEQ ID NO:41:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:41:

ACAGAAUCAA GUGUC 15

( 2 ) INFORMATION FOR SEQ ID NO:42:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:42:

CAAGUGUCCU UGCAA 15

( 2 ) INFORMATION FOR SEQ ID NO:43:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:43:

GUGUCCUUGC AACUC 15

( 2 ) INFORMATION FOR SEQ ID NO:44:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:44:

CCCAGAUCCA AGCAC 15

( 2 ) INFORMATION FOR SEQ ID NO:45:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:45:

GAGUUAUCGA GGCUC 15

( 2 ) INFORMATION FOR SEQ ID NO:46:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:46:

CUGGCAUCAG AGGAC 15

( 2 ) INFORMATION FOR SEQ ID NO:47:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:47:

ACAGAAUAUU AUCCA 15

( 2 ) INFORMATION FOR SEQ ID NO:48:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:48:

UUGGUGUUAU ACCAU 15

( 2 ) INFORMATION FOR SEQ ID NO:49:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:49:

GUGUUAUACC AUGGA 15

( 2 ) INFORMATION FOR SEQ ID NO:50:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:50:

CAUGGAUCCC AAUGU  15

(2) INFORMATION FOR SEQ ID NO:51:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:51:

ACAAUGUCCA GUGAC  15

(2) INFORMATION FOR SEQ ID NO:52:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:52:

GGCUGUUUCU GAACA  15

(2) INFORMATION FOR SEQ ID NO:53:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:53:

GCUGUUUCUG AACAA  15

(2) INFORMATION FOR SEQ ID NO:54:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:54:

CGAGGCUCAU UCUCC  15

(2) INFORMATION FOR SEQ ID NO:55:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:55:

GCUCAUUCUC CACCA  15

(2) INFORMATION FOR SEQ ID NO:56:

(i) SEQUENCE CHARACTERISTICS:
(A) LENGTH: 15 base pairs
(B) TYPE: nucleic acid (C) STRANDEDNESS: single
(D) TOPOLOGY: linear (x i) SEQUENCE DESCRIPTION: SEQ ID NO:56:

UCAUUCUCCA CCACU 15

(2) INFORMATION FOR SEQ ID NO:57:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:57:

CACUGUUACA GGAAG 15

(2) INFORMATION FOR SEQ ID NO:58:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:58:

CACAACUCCC ACGGU 15

(2) INFORMATION FOR SEQ ID NO:59:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:59:

UCCCAGUUCC AAGCA 15

(2) INFORMATION FOR SEQ ID NO:60:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:60:

CACCACUAUC ACAGG 15

(2) INFORMATION FOR SEQ ID NO:61:

(i) SEQUENCE CHARACTERISTICS:
(A) LENGTH: 15 base pairs
(B) TYPE: nucleic acid
(C) STRANDEDNESS: single
(D) TOPOLOGY: linear (x i) SEQUENCE DESCRIPTION: SEQ ID NO:61:

AACAUGUCAG UCUUG 15

(2) INFORMATION FOR SEQ ID NO:62:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:62:

ACCACAUUGG CAUCG 15

( 2 ) INFORMATION FOR SEQ ID NO:63:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

GUGUCCUCAC AACUC 15

( 2 ) INFORMATION FOR SEQ ID NO:64:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

CCCGGUUCCA AGCAC 15

( 2 ) INFORMATION FOR SEQ ID NO:65:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

CUAUGAUACC ACACU 15

( 2 ) INFORMATION FOR SEQ ID NO:66:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

UCCAGAUUCU GGGAA 15

( 2 ) INFORMATION FOR SEQ ID NO:67:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

CCAGAUUCUG GGAAA 15

( 2 ) INFORMATION FOR SEQ ID NO:68:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

ACAGAAUCAG GUGUC 15

(2) INFORMATION FOR SEQ ID NO:69:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:69:

CAGGUGUCCU AGAGA 15

(2) INFORMATION FOR SEQ ID NO:70:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:70:

GUGUCCUAGA GACUC 15

(2) INFORMATION FOR SEQ ID NO:71:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:71:

AGAGACUCCC ACUGU 15

(2) INFORMATION FOR SEQ ID NO:72:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:72:

GCUCAUUCUG AAGCA 15

(2) INFORMATION FOR SEQ ID NO:73:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:73:

GCACAUUCUC CACCA 15

(2) INFORMATION FOR SEQ ID NO:74:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:74:

GACAUGUCAA UCUUG 15

( 2 ) INFORMATION FOR SEQ ID NO:75:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

AGGCCCUUGG UGUUU 15

( 2 ) INFORMATION FOR SEQ ID NO:76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

CGAUGCUCAG ACACA 15

( 2 ) INFORMATION FOR SEQ ID NO:77:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

GCAUCCUCUU CAUUU 15

( 2 ) INFORMATION FOR SEQ ID NO:78:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

AUCCUCUUCA UUUGA 15

( 2 ) INFORMATION FOR SEQ ID NO:79:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

GCACCUUAAU AUCCC 15

( 2 ) INFORMATION FOR SEQ ID NO:80:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

CUCGAAUCUC AUGUU 15

( 2 ) INFORMATION FOR SEQ ID NO:81:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

CGAAUCUCAU GUUCA 15

( 2 ) INFORMATION FOR SEQ ID NO:82:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

UGGUAUUUUU GUGUA 15

( 2 ) INFORMATION FOR SEQ ID NO:83:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

UGUGUAUAAG CUUUU 15

( 2 ) INFORMATION FOR SEQ ID NO:84:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

ACUUAUUUUG AUUUG 15

( 2 ) INFORMATION FOR SEQ ID NO:85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

CUUAUUUUGA UUUGA 15

( 2 ) INFORMATION FOR SEQ ID NO:86:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

UGGUAGCCUG AUGAGGCCGA AAGGCCGAAA UCCUGG 36

( 2 ) INFORMATION FOR SEQ ID NO:87:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:87:

CCUCGAUCUG AUGAGGCCGA AAGGCCGAAA CUCUGU      36

( 2 ) INFORMATION FOR SEQ ID NO:88:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:88:

GUGCCUCCUG AUGAGGCCGA AAGGCCGAAA UAACUC      36

( 2 ) INFORMATION FOR SEQ ID NO:89:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:89:

GAUGACCCUG AUGAGGCCGA AAGGCCGAAA GCUUGG      36

( 2 ) INFORMATION FOR SEQ ID NO:90:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:90:

UGCGUCUCUG AUGAGGCCGA AAGGCCGAAA GCAUUG      36

( 2 ) INFORMATION FOR SEQ ID NO:91:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:91:

ACCGGGGCUG AUGAGGCCGA AAGGCCGAAA ACAGUC      36

( 2 ) INFORMATION FOR SEQ ID NO:92:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:92:

GGCUUGGCUG AUGAGGCCGA AAGGCCGAAA CCGGGG      36

( 2 ) INFORMATION FOR SEQ ID NO:93:

( i ) SEQUENCE CHARACTERISTICS:
    ( A ) LENGTH: 36 base pairs (B) TYPE: nucleic acid
            (C) STRANDEDNESS: single
            (D) TOPOLOGY: linear (xi) SEQUENCE DESCRIPTION: SEQ ID NO:93:

AGGCUUGCUG AUGAGGCCGA AAGGCCGAAA ACCGGG                                36

(2) INFORMATION FOR SEQ ID NO:94:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:94:

GAGCCUCCUG AUGAGGCCGA AAGGCCGAAA GGCUUG                                36

(2) INFORMATION FOR SEQ ID NO:95:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:95:

UGUCCAUCUG AUGAGGCCGA AAGGCCGAAA CCAUGG                                36

(2) INFORMATION FOR SEQ ID NO:96:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:96:

GGGGUCCCUG AUGAGGCCGA AAGGCCGAAA CUAUGC                                36

(2) INFORMATION FOR SEQ ID NO:97:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:97:

UGUCCAUCUG AUGAGGCCGA AAGGCCGAAA CCGUGG                                36

(2) INFORMATION FOR SEQ ID NO:98:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:98:

GCCACAGCUG AUGAGGCCGA AAGGCCGAAA UCUGGA                                36

(2) INFORMATION FOR SEQ ID NO:99:

(i) SEQUENCE CHARACTERISTICS:
            (A) LENGTH: 36 base pairs
            (B) TYPE: nucleic acid
            (C) STRANDEDNESS: single (D) TOPOLOGY: linear (x i) SEQUENCE DESCRIPTION: SEQ ID NO:99:

UAACAAUCUG AUGAGGCCGA AAGGCCGAAA GGGGCU 36

(2) INFORMATION FOR SEQ ID NO:100:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:100:

AUAACAACUG AUGAGGCCGA AAGGCCGAAA AGGGGC 36

(2) INFORMATION FOR SEQ ID NO:101:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:101:

GUAUAACCUG AUGAGGCCGA AAGGCCGAAA UAAGGG 36

(2) INFORMATION FOR SEQ ID NO:102:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:102:

UGUUCAGCUG AUGAGGCCGA AAGGCCGAAA GGAGCC 36

(2) INFORMATION FOR SEQ ID NO:103:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:103:

UUGUUCACUG AUGAGGCCGA AAGGCCGAAA AGGAGC 36

(2) INFORMATION FOR SEQ ID NO:104:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:104:

UCGGCAGCUG AUGAGGCCGA AAGGCCGAAA GUUCUU 36

(2) INFORMATION FOR SEQ ID NO:105:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:105:

GGAUCUGCUG AUGAGGCCGA AAGGCCGAAA UUUCGG 36

(2) INFORMATION FOR SEQ ID NO:106:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

UAACACCCUG AUGAGGCCGA AAGGCCGAAA GGGGCU 36

(2) INFORMATION FOR SEQ ID NO:107:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

GUUGUAUCUG AUGAGGCCGA AAGGCCGAAA CACCAA 36

(2) INFORMATION FOR SEQ ID NO:108:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:108:

UGCAUCUCUG AUGAGGCCGA AAGGCCGAAA GCAUCG 36

(2) INFORMATION FOR SEQ ID NO:109:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:109:

AAGCCUCCUG AUGAGGCCGA AAGGCCGAAA GGCUUG 36

(2) INFORMATION FOR SEQ ID NO:110:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:110:

UGUUCAACUG AUGAGGCCGA AAGGCCGAAA AAAGCC 36

(2) INFORMATION FOR SEQ ID NO:111:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:111:

```
AUAAUGGCUG  AUGAGGCCGA  AAGGCCGAAA  GUAGCA                                36
```

( 2 ) INFORMATION FOR SEQ ID NO:112:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:112:

```
UGUCCAUCUG  AUGAGGCCGA  AAGGCCGAAA  UGGUAG                                36
```

( 2 ) INFORMATION FOR SEQ ID NO:113:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:113:

```
CUGUCCACUG  AUGAGGCCGA  AAGGCCGAAA  AUGGUA                                36
```

( 2 ) INFORMATION FOR SEQ ID NO:114:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:114:

```
GCUUGGCCUG  AUGAGGCCGA  AAGGCCGAAA  GUUCUU                                36
```

( 2 ) INFORMATION FOR SEQ ID NO:115:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:115:

```
GUCCGACCUG  AUGAGGCCGA  AAGGCCGAAA  UGCUGG                                36
```

( 2 ) INFORMATION FOR SEQ ID NO:116:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:116:

```
AAGGGCGCUG  AUGAGGCCGA  AAGGCCGAAA  UCUCAG                                36
```

( 2 ) INFORMATION FOR SEQ ID NO:117:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:117:

```
CAAGGGCCUG  AUGAGGCCGA  AAGGCCGAAA  AUCUCA                                36
```

( 2 ) INFORMATION FOR SEQ ID NO:118:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:118:

UAACACCCUG AUGAGGCCGA AAGGCCGAAA GGGCGA     36

( 2 ) INFORMATION FOR SEQ ID NO:119:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:119:

ACACUGGCUG AUGAGGCCGA AAGGCCGAAA UCCAUG     36

( 2 ) INFORMATION FOR SEQ ID NO:120:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:120:

GACACUUCUG AUGAGGCCGA AAGGCCGAAA UUCUGU     36

( 2 ) INFORMATION FOR SEQ ID NO:121:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:121:

UUGCAAGCUG AUGAGGCCGA AAGGCCGAAA CACUUG     36

( 2 ) INFORMATION FOR SEQ ID NO:122:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:122:

GAGUUGCCUG AUGAGGCCGA AAGGCCGAAA GGACAC     36

( 2 ) INFORMATION FOR SEQ ID NO:123:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:123:

GUGCUUGCUG AUGAGGCCGA AAGGCCGAAA UCUGGG     36

( 2 ) INFORMATION FOR SEQ ID NO:124:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:124:

GAGCCUCCUG AUGAGGCCGA AAGGCCGAAA UAACUC 36

( 2 ) INFORMATION FOR SEQ ID NO:125:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:125:

GUCCUCUCUG AUGAGGCCGA AAGGCCGAAA UGCCAG 36

( 2 ) INFORMATION FOR SEQ ID NO:126:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:126:

UGGAUAACUG AUGAGGCCGA AAGGCCGAAA UUCUGU 36

( 2 ) INFORMATION FOR SEQ ID NO:127:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:127:

AUGGUAUCUG AUGAGGCCGA AAGGCCGAAA CACCAA 36

( 2 ) INFORMATION FOR SEQ ID NO:128:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:128:

UCCAUGGCUG AUGAGGCCGA AAGGCCGAAA UAACAC 36

( 2 ) INFORMATION FOR SEQ ID NO:129:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:129:

ACAUUGGCUG AUGAGGCCGA AAGGCCGAAA UCCAUG 36

( 2 ) INFORMATION FOR SEQ ID NO:130:

( i ) SEQUENCE CHARACTERISTICS:

(A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:130:

GUCACUGCUG AUGAGGCCGA AAGGCCGAAA CAUUGU                          36

(2) INFORMATION FOR SEQ ID NO:131:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:131:

UGUUCAGCUG AUGAGGCCGA AAGGCCGAAA ACAGCC                          36

(2) INFORMATION FOR SEQ ID NO:132:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:132:

UUGUUCACUG AUGAGGCCGA AAGGCCGAAA AACAGC                          36

(2) INFORMATION FOR SEQ ID NO:133:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:133:

GGAGAAUCUG AUGAGGCCGA AAGGCCGAAA GCCUCG                          36

(2) INFORMATION FOR SEQ ID NO:134:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:134:

UGGUGGACUG AUGAGGCCGA AAGGCCGAAA AUGAGC                          36

(2) INFORMATION FOR SEQ ID NO:135:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:135:

AGUGGUGCUG AUGAGGCCGA AAGGCCGAAA GAAUGA                          36

(2) INFORMATION FOR SEQ ID NO:136:

(i) SEQUENCE CHARACTERISTICS:
                (A) LENGTH: 36 base pairs
                (B) TYPE: nucleic acid ( C ) STRANDEDNESS: single
( D ) TOPOLOGY: linear ( x i ) SEQUENCE DESCRIPTION: SEQ ID NO:136:

CUUCCUGCUG AUGAGGCCGA AAGGCCGAAA ACAGUG 36

( 2 ) INFORMATION FOR SEQ ID NO:137:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:137:

ACCGUGGCUG AUGAGGCCGA AAGGCCGAAA GUUGUG 36

( 2 ) INFORMATION FOR SEQ ID NO:138:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:138:

UGCUUGGCUG AUGAGGCCGA AAGGCCGAAA CUGGGA 36

( 2 ) INFORMATION FOR SEQ ID NO:139:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:139:

CCUGUGACUG AUGAGGCCGA AAGGCCGAAA GUGGUG 36

( 2 ) INFORMATION FOR SEQ ID NO:140:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:140:

CAAGACUCUG AUGAGGCCGA AAGGCCGAAA CAUGUU 36

( 2 ) INFORMATION FOR SEQ ID NO:141:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:141:

CGAUGCCCUG AUGAGGCCGA AAGGCCGAAA UGUGGU 36

( 2 ) INFORMATION FOR SEQ ID NO:142:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:142:

GAGUUGUCUG AUGAGGCCGA AAGGCCGAAA GGACAC    36

( 2 ) INFORMATION FOR SEQ ID NO:143:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:143:

GUGCUUGCUG AUGAGGCCGA AAGGCCGAAA ACCGGG    36

( 2 ) INFORMATION FOR SEQ ID NO:144:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:144:

AGUGUGGCUG AUGAGGCCGA AAGGCCGAAA UCAUAG    36

( 2 ) INFORMATION FOR SEQ ID NO:145:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:145:

UUCCCAGCUG AUGAGGCCGA AAGGCCGAAA UCUGGA    36

( 2 ) INFORMATION FOR SEQ ID NO:146:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:146:

UUUCCCACUG AUGAGGCCGA AAGGCCGAAA AUCUGG    36

( 2 ) INFORMATION FOR SEQ ID NO:147:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:147:

GACACCUCUG AUGAGGCCGA AAGGCCGAAA UUCUGU    36

( 2 ) INFORMATION FOR SEQ ID NO:148:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:148:

UCUCUAGCUG AUGAGGCCGA AAGGCCGAAA CACCUG 36

( 2 ) INFORMATION FOR SEQ ID NO:149:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:149:

GAGUCUCCUG AUGAGGCCGA AAGGCCGAAA GGACAC 36

( 2 ) INFORMATION FOR SEQ ID NO:150:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:150:

ACAGUGGCUG AUGAGGCCGA AAGGCCGAAA GUCUCU 36

( 2 ) INFORMATION FOR SEQ ID NO:151:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:151:

UGCUUCACUG AUGAGGCCGA AAGGCCGAAA AUGAGC 36

( 2 ) INFORMATION FOR SEQ ID NO:152:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:152:

UGGUGGACUG AUGAGGCCGA AAGGCCGAAA AUGUGC 36

( 2 ) INFORMATION FOR SEQ ID NO:153:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:153:

CAAGAUUCUG AUGAGGCCGA AAGGCCGAAA CAUGUC 36

( 2 ) INFORMATION FOR SEQ ID NO:154:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:154:

AAACACCCUG AUGAGGCCGA AAGGCCGAAA GGGCCU 36

( 2 ) INFORMATION FOR SEQ ID NO:155:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:155:

UGUGUCUCUG AUGAGGCCGA AAGGCCGAAA GCAUCG      36

( 2 ) INFORMATION FOR SEQ ID NO:156:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:156:

AAAUGAACUG AUGAGGCCGA AAGGCCGAAA GGAUGC      36

( 2 ) INFORMATION FOR SEQ ID NO:157:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:157:

UCAAAUGCUG AUGAGGCCGA AAGGCCGAAA GAGGAU      36

( 2 ) INFORMATION FOR SEQ ID NO:158:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:158:

GGGAUAUCUG AUGAGGCCGA AAGGCCGAAA AGGUGC      36

( 2 ) INFORMATION FOR SEQ ID NO:159:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

AACAUGACUG AUGAGGCCGA AAGGCCGAAA UUCGAG      36

( 2 ) INFORMATION FOR SEQ ID NO:160:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

UGAACAUCUG AUGAGGCCGA AAGGCCGAAA GAUUCG      36

( 2 ) INFORMATION FOR SEQ ID NO:161:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:161:

UACACAACUG AUGAGGCCGA AAGGCCGAAA AUACCA  36

( 2 ) INFORMATION FOR SEQ ID NO:162:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:162:

AAAAGCUCUG AUGAGGCCGA AAGGCCGAAA UACACA  36

( 2 ) INFORMATION FOR SEQ ID NO:163:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:163:

CAAAUCACUG AUGAGGCCGA AAGGCCGAAA AUAAGU  36

( 2 ) INFORMATION FOR SEQ ID NO:164:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:164:

UCAAAUCCUG AUGAGGCCGA AAGGCCGAAA AAUAAG  36

( 2 ) INFORMATION FOR SEQ ID NO:165:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:165:

CUGCCGUCGC ACCUC  15

( 2 ) INFORMATION FOR SEQ ID NO:166:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:166:

CUGCCGUCGC ACCUC  15

( 2 ) INFORMATION FOR SEQ ID NO:167:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:167:

CUGCCGUCGC ACCUC     15

( 2 ) INFORMATION FOR SEQ ID NO:168:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:168:

CCCCGGUUCC AAGCC     15

( 2 ) INFORMATION FOR SEQ ID NO:169:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:169:

AGAGGCUCCU UCCGA     15

( 2 ) INFORMATION FOR SEQ ID NO:170:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:170:

GGCUCCUUCC GAACA     15

( 2 ) INFORMATION FOR SEQ ID NO:171:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:171:

GGCUCCUUCC GAACA     15

( 2 ) INFORMATION FOR SEQ ID NO:172:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:172:

GGCUCCUUCC GAACA     15

( 2 ) INFORMATION FOR SEQ ID NO:173:

( i ) SEQUENCE CHARACTERISTICS:
    ( A ) LENGTH: 15 base pairs ( B ) TYPE: nucleic acid
( C ) STRANDEDNESS: single
( D ) TOPOLOGY: linear ( x i ) SEQUENCE DESCRIPTION: SEQ ID NO:173:

GGCUCCUUCC GAACA                                                                                         15

( 2 ) INFORMATION FOR SEQ ID NO:174:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:174:

GCUCCUUCCG AACAA                                                                                         15

( 2 ) INFORMATION FOR SEQ ID NO:175:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:175:

ACAGAGUUAU CGAGG                                                                                         15

( 2 ) INFORMATION FOR SEQ ID NO:176:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:176:

GAGUUAUCGA GGCAC                                                                                         15

( 2 ) INFORMATION FOR SEQ ID NO:177:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:177:

CCACACUCUC AUAGU                                                                                         15

( 2 ) INFORMATION FOR SEQ ID NO:178:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:178:

CCACACUCUC AUAGU                                                                                         15

( 2 ) INFORMATION FOR SEQ ID NO:179:

( i ) SEQUENCE CHARACTERISTICS:
( A ) LENGTH: 15 base pairs
( B ) TYPE: nucleic acid
( C ) STRANDEDNESS: single (D) TOPOLOGY: linear (xi) SEQUENCE DESCRIPTION: SEQ ID NO:179:

AGAGGCUCCU UCUGA 15

(2) INFORMATION FOR SEQ ID NO:180:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:180:

AGAGGCUCCU UCUGA 15

(2) INFORMATION FOR SEQ ID NO:181:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:181:

GUGUUAUACA ACGGA 15

(2) INFORMATION FOR SEQ ID NO:182:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:182:

AACGGAUCCC AGUGU 15

(2) INFORMATION FOR SEQ ID NO:183:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:183:

AGAGGCUUUU CUUGA 15

(2) INFORMATION FOR SEQ ID NO:184:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:184:

AGAGGCUUUU CUUGA 15

(2) INFORMATION FOR SEQ ID NO:185:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:185:

GAGGCUUUUC UUGAA 15

( 2 ) INFORMATION FOR SEQ ID NO:186:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:186:

AGGCUUUUCU UGAAC 15

( 2 ) INFORMATION FOR SEQ ID NO:187:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:187:

UGCUACUACC AUUAU 15

( 2 ) INFORMATION FOR SEQ ID NO:188:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:188:

GGCACAUACU CCACC 15

( 2 ) INFORMATION FOR SEQ ID NO:189:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:189:

CCACUGUUAC AGGAA 15

( 2 ) INFORMATION FOR SEQ ID NO:190:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:190:

CCACUGUUAC AGGAA 15

( 2 ) INFORMATION FOR SEQ ID NO:191:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:191:

CCACUGUUAC AGGAA 15

( 2 ) INFORMATION FOR SEQ ID NO:192:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:192:

CCACUGUUAC AGGAA 15

( 2 ) INFORMATION FOR SEQ ID NO:193:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:193:

CACUGUUACA GGAAG 15

( 2 ) INFORMATION FOR SEQ ID NO:194:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:194:

GCAUAGUCGG ACCCC 15

( 2 ) INFORMATION FOR SEQ ID NO:195:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:195:

GCAUAGUCGG ACCCC 15

( 2 ) INFORMATION FOR SEQ ID NO:196:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:196:

GCAUAGUCGG ACCCC 15

( 2 ) INFORMATION FOR SEQ ID NO:197:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:197:

AAAAACUAUC CAAAU 15

( 2 ) INFORMATION FOR SEQ ID NO:198:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:198:

CAGGAAUCCA GAUGC 15

( 2 ) INFORMATION FOR SEQ ID NO:199:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:199:

CAGGAAUCCA GAUGC 15

( 2 ) INFORMATION FOR SEQ ID NO:200:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:200:

CAGGAAUCCA GAUGC 15

( 2 ) INFORMATION FOR SEQ ID NO:201:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:201:

CAGGAAUCCA GAUGC 15

( 2 ) INFORMATION FOR SEQ ID NO:202:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

CAGGAAUCCA GAUGC 15

( 2 ) INFORMATION FOR SEQ ID NO:203:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

UCGCCCUUGG UGUUA 15

( 2 ) INFORMATION FOR SEQ ID NO:204:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:204:

ACAAUGUCUG GUGAC　　　　　　　　　　　　　　　　　　　　　　　15

( 2 ) INFORMATION FOR SEQ ID NO:205:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:205:

ACAGAAUCAA GUGUC　　　　　　　　　　　　　　　　　　　　　　　15

( 2 ) INFORMATION FOR SEQ ID NO:206:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:206:

GCUUCUUCUG AAGAA　　　　　　　　　　　　　　　　　　　　　　　15

( 2 ) INFORMATION FOR SEQ ID NO:207:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:207:

GACUGCUACC AUGGU　　　　　　　　　　　　　　　　　　　　　　　15

( 2 ) INFORMATION FOR SEQ ID NO:208:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:208:

GAGUUAUCGA GGCUC　　　　　　　　　　　　　　　　　　　　　　　15

( 2 ) INFORMATION FOR SEQ ID NO:209:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:209:

CGAGGCUCAU UCUCC　　　　　　　　　　　　　　　　　　　　　　　15

( 2 ) INFORMATION FOR SEQ ID NO:210:

( i ) SEQUENCE CHARACTERISTICS:

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:210:

UCAUUCUCCA CCACU 15

( 2 ) INFORMATION FOR SEQ ID NO:211:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:211:

GACAUGUCAG UCUUG 15

( 2 ) INFORMATION FOR SEQ ID NO:212:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:212:

UCUUGGUCCU CUAUG 15

( 2 ) INFORMATION FOR SEQ ID NO:213:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:213:

UGGUCCUCUA UGACA 15

( 2 ) INFORMATION FOR SEQ ID NO:214:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:214:

UGGUCCUCUA UGACA 15

( 2 ) INFORMATION FOR SEQ ID NO:215:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:215:

GUCCUCUAUG ACACC 15

( 2 ) INFORMATION FOR SEQ ID NO:216:

( i ) SEQUENCE CHARACTERISTICS:
( A ) LENGTH: 15 base pairs
( B ) TYPE: nucleic acid (C) STRANDEDNESS: single
(D) TOPOLOGY: linear (xi) SEQUENCE DESCRIPTION: SEQ ID NO:216:

AUAGAAUACU ACCCA                                    15

(2) INFORMATION FOR SEQ ID NO:217:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:217:

AUAGAAUACU ACCCA                                    15

(2) INFORMATION FOR SEQ ID NO:218:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:218:

AUGGAAUCAA GUGUC                                    15

(2) INFORMATION FOR SEQ ID NO:219:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:219:

CAAGUGUCCU UGCAA                                    15

(2) INFORMATION FOR SEQ ID NO:220:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:220:

UCCCAGUUCC AAGCA                                    15

(2) INFORMATION FOR SEQ ID NO:221:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO:221:

UCGGCAUCGG AGGAU                                    15

(2) INFORMATION FOR SEQ ID NO:222:

(i) SEQUENCE CHARACTERISTICS:
       (A) LENGTH: 15 base pairs
       (B) TYPE: nucleic acid
       (C) STRANDEDNESS: single
       (D) TOPOLOGY: linear ( x i ) SEQUENCE DESCRIPTION: SEQ ID NO:222:

U C C C A U U A C G   C U A U C                                                                    15

( 2 ) INFORMATION FOR SEQ ID NO:223:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:223:

G C U C C U U C U G   A A C A A                                                                    15

( 2 ) INFORMATION FOR SEQ ID NO:224:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:224:

C C A G G A U U G C   U A C C A                                                                    15

( 2 ) INFORMATION FOR SEQ ID NO:225:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:225:

C C A G G A U U G C   U A C C A                                                                    15

( 2 ) INFORMATION FOR SEQ ID NO:226:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:226:

G A A C U G U C A G   U C U U G                                                                    15

( 2 ) INFORMATION FOR SEQ ID NO:227:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:227:

U C U U G G U C A U   C U A U G                                                                    15

( 2 ) INFORMATION FOR SEQ ID NO:228:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:228:

UGGUCAUCUA UGAUA 15

( 2 ) INFORMATION FOR SEQ ID NO:229:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:229:

GUCAUCUAUG AUACC 15

( 2 ) INFORMATION FOR SEQ ID NO:230:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:230:

UGGUGUUACA CGACU 15

( 2 ) INFORMATION FOR SEQ ID NO:231:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:231:

AGAGACUCCC ACUGU 15

( 2 ) INFORMATION FOR SEQ ID NO:232:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:232:

CUGUUGUUCC GGUUC 15

( 2 ) INFORMATION FOR SEQ ID NO:233:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:233:

GCUCAUUCUG AAGCA 15

( 2 ) INFORMATION FOR SEQ ID NO:234:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:234:

UCAAUCUUGG UCAUC 15

( 2 ) INFORMATION FOR SEQ ID NO:235:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:235:

CCACAUUCCU GGCCC 15

( 2 ) INFORMATION FOR SEQ ID NO:236:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:236:

GGCAAGUCAG UCUUA 15

( 2 ) INFORMATION FOR SEQ ID NO:237:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:237:

AGGCCUUCCU UCUAC 15

( 2 ) INFORMATION FOR SEQ ID NO:238:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:238:

AGUGUCUAGG UUGUU 15

( 2 ) INFORMATION FOR SEQ ID NO:239:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:239:

AGUGUCUAGG UUGUU 15

( 2 ) INFORMATION FOR SEQ ID NO:240:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:240:

UGGUAUUAUU GUGUA 15

( 2 ) INFORMATION FOR SEQ ID NO:241:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:241:

UAAGCUUUUC CCGUC    15

( 2 ) INFORMATION FOR SEQ ID NO:242:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:242:

GAGGUGCCUG AUGAGGCCGA AAGGCCGAAA CGGCAG    36

( 2 ) INFORMATION FOR SEQ ID NO:243:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:243:

GAGGUGCCUG AUGAGGCCGA AAGGCCGAAA CGGCAG    36

( 2 ) INFORMATION FOR SEQ ID NO:244:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:244:

GAGGUGCCUG AUGAGGCCGA AAGGCCGAAA CGGCAG    36

( 2 ) INFORMATION FOR SEQ ID NO:245:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:245:

GGCUUGGCUG AUGAGGCCGA AAGGCCGAAA CCGGGG    36

( 2 ) INFORMATION FOR SEQ ID NO:246:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:246:

UCGGAAGCUG AUGAGGCCGA AAGGCCGAAA GCCUCU    36

( 2 ) INFORMATION FOR SEQ ID NO:247:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:247:

UGUUCGGCUG AUGAGGCCGA AAGGCCGAAA GGAGCC    36

(2) INFORMATION FOR SEQ ID NO:248:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:248:

UGUUCGGCUG AUGAGGCCGA AAGGCCGAAA GGAGCC    36

(2) INFORMATION FOR SEQ ID NO:249:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:249:

UGUUCGGCUG AUGAGGCCGA AAGGCCGAAA GGAGCC    36

(2) INFORMATION FOR SEQ ID NO:250:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:250:

UGUUCGGCUG AUGAGGCCGA AAGGCCGAAA GGAGCC    36

(2) INFORMATION FOR SEQ ID NO:251:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:251:

UUGUUCGCUG AUGAGGCCGA AAGGCCGAAA AGGAGC    36

(2) INFORMATION FOR SEQ ID NO:252:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:252:

CCUCGAUCUG AUGAGGCCGA AAGGCCGAAA CUCUGU    36

(2) INFORMATION FOR SEQ ID NO:253:

(i) SEQUENCE CHARACTERISTICS:
    (A) LENGTH: 36 base pairs (B) TYPE: nucleic acid
                (C) STRANDEDNESS: single
                (D) TOPOLOGY: linear (xi) SEQUENCE DESCRIPTION: SEQ ID NO:253:

GUGCCUCCUG AUGAGGCCGA AAGGCCGAAA UAACUC    36

(2) INFORMATION FOR SEQ ID NO:254:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:254:

ACUAUGACUG AUGAGGCCGA AAGGCCGAAA GUGUGG    36

(2) INFORMATION FOR SEQ ID NO:255:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:255:

ACUAUGACUG AUGAGGCCGA AAGGCCGAAA GUGUGG    36

(2) INFORMATION FOR SEQ ID NO:256:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:256:

UCAGAAGCUG AUGAGGCCGA AAGGCCGAAA GCCUCU    36

(2) INFORMATION FOR SEQ ID NO:257:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:257:

UCAGAAGCUG AUGAGGCCGA AAGGCCGAAA GCCUCU    36

(2) INFORMATION FOR SEQ ID NO:258:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (xi) SEQUENCE DESCRIPTION: SEQ ID NO:258:

UCCGUUGCUG AUGAGGCCGA AAGGCCGAAA UAACAC    36

(2) INFORMATION FOR SEQ ID NO:259:

(i) SEQUENCE CHARACTERISTICS:
                (A) LENGTH: 36 base pairs
                (B) TYPE: nucleic acid
                (C) STRANDEDNESS: single (D) TOPOLOGY: linear (xi) SEQUENCE DESCRIPTION: SEQ ID NO:259:

ACACUGGCUG AUGAGGCCGA AAGGCCGAAA UCCGUU 36

(2) INFORMATION FOR SEQ ID NO:260:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:260:

UCAAGAACUG AUGAGGCCGA AAGGCCGAAA GCCUCU 36

(2) INFORMATION FOR SEQ ID NO:261:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:261:

UCAAGAACUG AUGAGGCCGA AAGGCCGAAA GCCUCU 36

(2) INFORMATION FOR SEQ ID NO:262:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:262:

UUCAAGACUG AUGAGGCCGA AAGGCCGAAA AGCCUC 36

(2) INFORMATION FOR SEQ ID NO:263:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:263:

GUUCAAGCUG AUGAGGCCGA AAGGCCGAAA AAGCCU 36

(2) INFORMATION FOR SEQ ID NO:264:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:264:

AUAAUGGCUG AUGAGGCCGA AAGGCCGAAA GUAGCA 36

(2) INFORMATION FOR SEQ ID NO:265:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:265:

GGUGGAGCUG AUGAGGCCGA AAGGCCGAAA UGUGCC 36

(2) INFORMATION FOR SEQ ID NO:266:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:266:

UUCCUGUCUG AUGAGGCCGA AAGGCCGAAA CAGUGG 36

(2) INFORMATION FOR SEQ ID NO:267:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:267:

UUCCUGUCUG AUGAGGCCGA AAGGCCGAAA CAGUGG 36

(2) INFORMATION FOR SEQ ID NO:268:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:268:

UUCCUGUCUG AUGAGGCCGA AAGGCCGAAA CAGUGG 36

(2) INFORMATION FOR SEQ ID NO:269:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:269:

UUCCUGUCUG AUGAGGCCGA AAGGCCGAAA CAGUGG 36

(2) INFORMATION FOR SEQ ID NO:270:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:270:

CUUCCUGCUG AUGAGGCCGA AAGGCCGAAA ACAGUG 36

(2) INFORMATION FOR SEQ ID NO:271:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (x i) SEQUENCE DESCRIPTION: SEQ ID NO:271:

```
        GGGGUCCCUG  AUGAGGCCGA  AAGGCCGAAA  CUAUGC                              36
```

( 2 ) INFORMATION FOR SEQ ID NO:272:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:272:

```
        GGGGUCCCUG  AUGAGGCCGA  AAGGCCGAAA  CUAUGC                              36
```

( 2 ) INFORMATION FOR SEQ ID NO:273:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:273:

```
        GGGGUCCCUG  AUGAGGCCGA  AAGGCCGAAA  CUAUGC                              36
```

( 2 ) INFORMATION FOR SEQ ID NO:274:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:274:

```
        AUUUGGACUG  AUGAGGCCGA  AAGGCCGAAA  GUUUUU                              36
```

( 2 ) INFORMATION FOR SEQ ID NO:275:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:275:

```
        GCAUCUGCUG  AUGAGGCCGA  AAGGCCGAAA  UUCCUG                              36
```

( 2 ) INFORMATION FOR SEQ ID NO:276:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:276:

```
        GCAUCUGCUG  AUGAGGCCGA  AAGGCCGAAA  UUCCUG                              36
```

( 2 ) INFORMATION FOR SEQ ID NO:277:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:277:

```
        GCAUCUGCUG  AUGAGGCCGA  AAGGCCGAAA  UUCCUG                              36
```

( 2 ) INFORMATION FOR SEQ ID NO:278:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:278:

GCAUCUGCUG AUGAGGCCGA AAGGCCGAAA UUCCUG  36

( 2 ) INFORMATION FOR SEQ ID NO:279:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:279:

GCAUCUGCUG AUGAGGCCGA AAGGCCGAAA UUCCUG  36

( 2 ) INFORMATION FOR SEQ ID NO:280:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:280:

UAACACCCUG AUGAGGCCGA AAGGCCGAAA GGGCGA  36

( 2 ) INFORMATION FOR SEQ ID NO:281:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:281:

GUCACCACUG AUGAGGCCGA AAGGCCGAAA CAUUGU  36

( 2 ) INFORMATION FOR SEQ ID NO:282:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:282:

GACACUUCUG AUGAGGCCGA AAGGCCGAAA UUCUGU  36

( 2 ) INFORMATION FOR SEQ ID NO:283:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:283:

UUCUUCACUG AUGAGGCCGA AAGGCCGAAA AGAAGC  36

( 2 ) INFORMATION FOR SEQ ID NO:284:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:284:

ACCAUGGCUG AUGAGGCCGA AAGGCCGAAA GCAGUC 36

( 2 ) INFORMATION FOR SEQ ID NO:285:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:285:

GAGCCUCCUG AUGAGGCCGA AAGGCCGAAA UAACUC 36

( 2 ) INFORMATION FOR SEQ ID NO:286:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:286:

GGAGAAUCUG AUGAGGCCGA AAGGCCGAAA GCCUCG 36

( 2 ) INFORMATION FOR SEQ ID NO:287:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:287:

AGUGGUGCUG AUGAGGCCGA AAGGCCGAAA GAAUGA 36

( 2 ) INFORMATION FOR SEQ ID NO:288:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:288:

CAAGACUCUG AUGAGGCCGA AAGGCCGAAA CAUGUC 36

( 2 ) INFORMATION FOR SEQ ID NO:289:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:289:

CAUAGAGCUG AUGAGGCCGA AAGGCCGAAA CCAAGA 36

( 2 ) INFORMATION FOR SEQ ID NO:290:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:290:

UGUCAUACUG AUGAGGCCGA AAGGCCGAAA GGACCA 36

(2) INFORMATION FOR SEQ ID NO:291:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:291:

UGUCAUACUG AUGAGGCCGA AAGGCCGAAA GGACCA 36

(2) INFORMATION FOR SEQ ID NO:292:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:292:

GGUGUCACUG AUGAGGCCGA AAGGCCGAAA GAGGAC 36

(2) INFORMATION FOR SEQ ID NO:293:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:293:

UGGGUAGCUG AUGAGGCCGA AAGGCCGAAA UUCUAU 36

(2) INFORMATION FOR SEQ ID NO:294:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:294:

UGGGUAGCUG AUGAGGCCGA AAGGCCGAAA UUCUAU 36

(2) INFORMATION FOR SEQ ID NO:295:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:295:

GACACUUCUG AUGAGGCCGA AAGGCCGAAA UUCCAU 36

(2) INFORMATION FOR SEQ ID NO:296:

(i) SEQUENCE CHARACTERISTICS:
(A) LENGTH: 36 base pairs
(B) TYPE: nucleic acid (C) STRANDEDNESS: single
(D) TOPOLOGY: linear (xi) SEQUENCE DESCRIPTION: SEQ ID NO:296:

UUGCAAGCUG AUGAGGCCGA AAGGCCGAAA CACUUG    36

(2) INFORMATION FOR SEQ ID NO:297:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:297:

UGCUUGGCUG AUGAGGCCGA AAGGCCGAAA CUGGGA    36

(2) INFORMATION FOR SEQ ID NO:298:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:298:

AUCCUCCCUG AUGAGGCCGA AAGGCCGAAA UGCCGA    36

(2) INFORMATION FOR SEQ ID NO:299:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:299:

GAUAGCGCUG AUGAGGCCGA AAGGCCGAAA AUGGGA    36

(2) INFORMATION FOR SEQ ID NO:300:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:300:

UUGUUCACUG AUGAGGCCGA AAGGCCGAAA AGGAGC    36

(2) INFORMATION FOR SEQ ID NO:301:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:301:

UGGUAGCCUG AUGAGGCCGA AAGGCCGAAA UCCUGG    36

(2) INFORMATION FOR SEQ ID NO:302:

(i) SEQUENCE CHARACTERISTICS:
    (A) LENGTH: 36 base pairs
    (B) TYPE: nucleic acid
    (C) STRANDEDNESS: single
    (D) TOPOLOGY: linear ( x i ) SEQUENCE DESCRIPTION: SEQ ID NO:302:

UGGUAGCCUG AUGAGGCCGA AAGGCCGAAA UCCUGG 36

( 2 ) INFORMATION FOR SEQ ID NO:303:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:303:

CAAGACUCUG AUGAGGCCGA AAGGCCGAAA CAGUUC 36

( 2 ) INFORMATION FOR SEQ ID NO:304:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:304:

CAUAGAUCUG AUGAGGCCGA AAGGCCGAAA CCAAGA 36

( 2 ) INFORMATION FOR SEQ ID NO:305:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:305:

UAUCAUACUG AUGAGGCCGA AAGGCCGAAA UGACCA 36

( 2 ) INFORMATION FOR SEQ ID NO:306:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:306:

GGUAUCACUG AUGAGGCCGA AAGGCCGAAA GAUGAC 36

( 2 ) INFORMATION FOR SEQ ID NO:307:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:307:

AGUCGUGCUG AUGAGGCCGA AAGGCCGAAA ACACCA 36

( 2 ) INFORMATION FOR SEQ ID NO:308:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:308:

ACAGUGGCUG AUGAGGCCGA AAGGCCGAAA GUCUCU 36

(2) INFORMATION FOR SEQ ID NO:309:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:309:

GAACCGGCUG AUGAGGCCGA AAGGCCGAAA CAACAG 36

(2) INFORMATION FOR SEQ ID NO:310:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:310:

UGCUUCACUG AUGAGGCCGA AAGGCCGAAA AUGAGC 36

(2) INFORMATION FOR SEQ ID NO:311:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:311:

GAUGACCCUG AUGAGGCCGA AAGGCCGAAA GAUUGA 36

(2) INFORMATION FOR SEQ ID NO:312:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:312:

GGGCCAGCUG AUGAGGCCGA AAGGCCGAAA AUGUGG 36

(2) INFORMATION FOR SEQ ID NO:313:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:313:

UAAGACUCUG AUGAGGCCGA AAGGCCGAAA CUUGCC 36

(2) INFORMATION FOR SEQ ID NO:314:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:314:

GUAGAAGCUG AUGAGGCCGA AAGGCCGAAA AGGCCU 36

( 2 ) INFORMATION FOR SEQ ID NO:315:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:315:

AACAACCCUG AUGAGGCCGA AAGGCCGAAA GACACU     36

( 2 ) INFORMATION FOR SEQ ID NO:316:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:316:

AACAACCCUG AUGAGGCCGA AAGGCCGAAA GACACU     36

( 2 ) INFORMATION FOR SEQ ID NO:317:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:317:

UACACAACUG AUGAGGCCGA AAGGCCGAAA AUACCA     36

( 2 ) INFORMATION FOR SEQ ID NO:318:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:318:

GACGGGACUG AUGAGGCCGA AAGGCCGAAA AGCUUA     36

( 2 ) INFORMATION FOR SEQ ID NO:319:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:319:

GGCGCGACAG AAGUCCACCA GAGAAACACA CGUUGUGGUA CAUUACCUGG UA     52

( 2 ) INFORMATION FOR SEQ ID NO:320:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:320:

GGAGGCGCAG AAGCAGACCA GAGAAACACA CGUUGUGGUA CAUUACCUGG UA     52

( 2 ) INFORMATION FOR SEQ ID NO:321:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:321:

UUUGCUCAAG AAGUGCACCA GAGAAACACA CGUUGUGGUA CAUUACCUGG UA    52

( 2 ) INFORMATION FOR SEQ ID NO:322:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:322:

UCUGCUCAAG AAGUGCACCA GAGAAACACA CGUUGUGGUA CAUUACCUGG UA    52

( 2 ) INFORMATION FOR SEQ ID NO:323:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:323:

CAAUAAGGAG AAGCCAACCA GAGAAACACA CGUUGUGGUA CAUUACCUGG UA    52

( 2 ) INFORMATION FOR SEQ ID NO:324:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:324:

UGGAUUUCAG AAGUAGACCA GAGAAACACA CGUUGUGGUA CAUUACCUGG UA    52

( 2 ) INFORMATION FOR SEQ ID NO:325:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:325:

CACCAAGGAG AAGCCAACCA GAGAAACACA CGUUGUGGUA CAUUACCUGG UA    52

( 2 ) INFORMATION FOR SEQ ID NO:326:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:326:

GGGACGAAAG AAGUCCACCA GAGAAACACA CGUUGUGGUA CAUUACCUGG UA    52

( 2 ) INFORMATION FOR SEQ ID NO:327:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:327:

UUUCCUCAAG AAGUGCACCA GAGAAACACA CGUUGUGGUA CAUUACCUGG UA    5 2

( 2 ) INFORMATION FOR SEQ ID NO:328:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:328:

UGUUCAGAAG AAGCCGACCA GAGAAACACA CGUUGUGGUA CAUUACCUGG UA    5 2

( 2 ) INFORMATION FOR SEQ ID NO:329:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:329:

CAGUCCUGAG AAGUGGACCA GAGAAACACA CGUUGUGGUA CAUUACCUGG UA    5 2

( 2 ) INFORMATION FOR SEQ ID NO:330:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:330:

ACUGGAACAG AAGUGGACCA GAGAAACACA CGUUGUGGUA CAUUACCUGG UA    5 2

( 2 ) INFORMATION FOR SEQ ID NO:331:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:331:

GGCUCCUGAG AAGCCCACCA GAGAAACACA CGUUGUGGUA CAUUACCUGG UA    5 2

( 2 ) INFORMATION FOR SEQ ID NO:332:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:332:

AGGGUUACAG AAGUAAACCA GAGAAACACA CGUUGUGGUA CAUUACCUGG UA    5 2

( 2 ) INFORMATION FOR SEQ ID NO:333:

( i ) SEQUENCE CHARACTERISTICS:
  ( A ) LENGTH: 52 base pairs (B) TYPE: nucleic acid
(C) STRANDEDNESS: single
(D) TOPOLOGY: linear (x i) SEQUENCE DESCRIPTION: SEQ ID NO:333:

GAGCAGCAAG AAGCACACCA GAGAAACACA CGUUGUGGUA CAUUACCUGG UA 52

(2) INFORMATION FOR SEQ ID NO:334:

(i) SEQUENCE CHARACTERISTICS:
(A) LENGTH: 52 base pairs
(B) TYPE: nucleic acid
(C) STRANDEDNESS: single
(D) TOPOLOGY: linear (x i) SEQUENCE DESCRIPTION: SEQ ID NO:334:

GCUCCAAGAG AAGCCUACCA GAGAAACACA CGUUGUGGUA CAUUACCUGG UA 52

(2) INFORMATION FOR SEQ ID NO:335:

(i) SEQUENCE CHARACTERISTICS:
(A) LENGTH: 52 base pairs
(B) TYPE: nucleic acid
(C) STRANDEDNESS: single
(D) TOPOLOGY: linear (x i) SEQUENCE DESCRIPTION: SEQ ID NO:335:

ACCCUGGCAG AAGUCAACCA GAGAAACACA CGUUGUGGUA CAUUACCUGG UA 52

(2) INFORMATION FOR SEQ ID NO:336:

(i) SEQUENCE CHARACTERISTICS:
(A) LENGTH: 52 base pairs
(B) TYPE: nucleic acid
(C) STRANDEDNESS: single
(D) TOPOLOGY: linear (x i) SEQUENCE DESCRIPTION: SEQ ID NO:336:

UAGCUGGGAG AAGUGUACCA GAGAAACACA CGUUGUGGUA CAUUACCUGG UA 52

(2) INFORMATION FOR SEQ ID NO:337:

(i) SEQUENCE CHARACTERISTICS:
(A) LENGTH: 16 base pairs
(B) TYPE: nucleic acid
(C) STRANDEDNESS: single
(D) TOPOLOGY: linear (x i) SEQUENCE DESCRIPTION: SEQ ID NO:337:

GGACUGCCGU CGCGCC 16

(2) INFORMATION FOR SEQ ID NO:338:

(i) SEQUENCE CHARACTERISTICS:
(A) LENGTH: 16 base pairs
(B) TYPE: nucleic acid
(C) STRANDEDNESS: single
(D) TOPOLOGY: linear (x i) SEQUENCE DESCRIPTION: SEQ ID NO:338:

CUGCCGUCGC GCCUCC 16

(2) INFORMATION FOR SEQ ID NO:339:

(i) SEQUENCE CHARACTERISTICS:
(A) LENGTH: 16 base pairs
(B) TYPE: nucleic acid
(C) STRANDEDNESS: single (D) TOPOLOGY: linear (xi) SEQUENCE DESCRIPTION: SEQ ID NO:339:

GCACCGACUG AGCAAA 16

(2) INFORMATION FOR SEQ ID NO:340:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:340:

GCACCGACUG AGCAGA 16

(2) INFORMATION FOR SEQ ID NO:341:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:341:

UGGCAGCCCC UUAUUG 16

(2) INFORMATION FOR SEQ ID NO:342:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:342:

CUACUGCCGA AAUCCA 16

(2) INFORMATION FOR SEQ ID NO:343:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:343:

UGGCAGCCCC UUGGUG 16

(2) INFORMATION FOR SEQ ID NO:344:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:344:

GGACUGCCUU CGUCCC 16

(2) INFORMATION FOR SEQ ID NO:345:

(i) SEQUENCE CHARACTERISTICS:
(A) LENGTH: 16 base pairs
(B) TYPE: nucleic acid
(C) STRANDEDNESS: single
(D) TOPOLOGY: linear ( x i ) SEQUENCE DESCRIPTION: SEQ ID NO:345:

GCACUGACUG AGGAAA  16

( 2 ) INFORMATION FOR SEQ ID NO:346:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:346:

CGGCUGUUUC UGAACA  16

( 2 ) INFORMATION FOR SEQ ID NO:347:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:347:

CCACAGUCCA GGACUG  16

( 2 ) INFORMATION FOR SEQ ID NO:348:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:348:

CCACUGUUGU UCCAGU  16

( 2 ) INFORMATION FOR SEQ ID NO:349:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:349:

GGGCUGCCCA GGAGCC  16

( 2 ) INFORMATION FOR SEQ ID NO:350:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:350:

UUACUGCCGU AACCCU  16

( 2 ) INFORMATION FOR SEQ ID NO:351:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:351:

```
GUGCUGACUG CUGCUC                                                                          16
```

( 2 ) INFORMATION FOR SEQ ID NO:352:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:352:

```
AGGCUGUUCU UGGAGC                                                                          16
```

( 2 ) INFORMATION FOR SEQ ID NO:353:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:353:

```
UGACAGUUGC CAGGGU                                                                          16
```

( 2 ) INFORMATION FOR SEQ ID NO:354:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:354:

```
ACACUGUUCC CAGCUA                                                                          16
```

( 2 ) INFORMATION FOR SEQ ID NO:355:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:355:

```
GGUGCGACAG AAGUCCACCA GAGAAACACA CGUUGUGGUA CAUUACCUGG UA                                  52
```

( 2 ) INFORMATION FOR SEQ ID NO:356:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:356:

```
GGAGGUGCAG AAGCAGACCA GAGAAACACA CGUUGUGGUA CAUUACCUGG UA                                  52
```

( 2 ) INFORMATION FOR SEQ ID NO:357:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:357:

```
UUUGCUCAAG AAGUGCACCA GAGAAACACA CGUUGUGGUA CAUUACCUGG UA                                  52
```

( 2 ) INFORMATION FOR SEQ ID NO:358:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:358:

CAAUAAGGAG AAGCCAACCA GAGAAACACA CGUUGUGGUA CAUUACCUGG UA    52

( 2 ) INFORMATION FOR SEQ ID NO:359:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:359:

CAAUAAGGAG AAGCCAACCA GAGAAACACA CGUUGUGGUA CAUUACCUGG UA    52

( 2 ) INFORMATION FOR SEQ ID NO:360:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:360:

GGAGGUGCAG AAGCAGACCA GAGAAACACA CGUUGUGGUA CAUUACCUGG UA    52

( 2 ) INFORMATION FOR SEQ ID NO:361:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:361:

UUUGCUCAAG AAGUGCACCA GAGAAACACA CGUUGUGGUA CAUUACCUGG UA    52

( 2 ) INFORMATION FOR SEQ ID NO:362:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:362:

CAAUAAGGAG AAGCCAACCA GAGAAACACA CGUUGUGGUA CAUUACCUGG UA    52

( 2 ) INFORMATION FOR SEQ ID NO:363:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:363:

GGUGCGACAG AAGUCCACCA GAGAAACACA CGUUGUGGUA CAUUACCUGG UA    52

( 2 ) INFORMATION FOR SEQ ID NO:364:

( i ) SEQUENCE CHARACTERISTICS:
  ( A ) LENGTH: 52 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:364:

GGAGGUGCAG AAGCAGACCA GAGAAACACA CGUUGUGGUA CAUUACCUGG UA        52

( 2 ) INFORMATION FOR SEQ ID NO:365:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:365:

UGGAUUUCAG AAGUAGACCA GAGAAACACA CGUUGUGGUA CAUUACCUGG UA        52

( 2 ) INFORMATION FOR SEQ ID NO:366:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:366:

CACCAAGGAG AAGCCAACCA GAGAAACACA CGUUGUGGUA CAUUACCUGG UA        52

( 2 ) INFORMATION FOR SEQ ID NO:367:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:367:

UGUUCAGAAG AAGCCAACCA GAGAAACACA CGUUGUGGUA CAUUACCUGG UA        52

( 2 ) INFORMATION FOR SEQ ID NO:368:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:368:

GACCCCAGAG AAGUUUACCA GAGAAACACA CGUUGUGGUA CAUUACCUGG UA        52

( 2 ) INFORMATION FOR SEQ ID NO:369:

( i ) SEQUENCE CHARACTERISTICS:
    ( A ) LENGTH: 52 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:369:

ACCGGAACAG AAGUGGACCA GAGAAACACA CGUUGUGGUA CAUUACCUGG UA        52

( 2 ) INFORMATION FOR SEQ ID NO:370:

( i ) SEQUENCE CHARACTERISTICS:

(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:370:

AAGCAGCAAG AAGCACACCA GAGAAACACA CGUUGUGGUA CAUUACCUGG UA 52

(2) INFORMATION FOR SEQ ID NO:371:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:371:

AAUUUGGAAG AAGCAGACCA GAGAAACACA CGUUGUGGUA CAUUACCUGG UA 52

(2) INFORMATION FOR SEQ ID NO:372:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:372:

UCAGUCCAAG AAGUGAACCA GAGAAACACA CGUUGUGGUA CAUUACCUGG UA 52

(2) INFORMATION FOR SEQ ID NO:373:

(i) SEQUENCE CHARACTERISTICS:
(A) LENGTH: 52 base pairs
(B) TYPE: nucleic acid
(C) STRANDEDNESS: single
(D) TOPOLOGY: linear (xi) SEQUENCE DESCRIPTION: SEQ ID NO:373:

UAGCUGGGAG AAGUGUACCA GAGAAACACA CGUUGUGGUA CAUUACCUGG UA 52

(2) INFORMATION FOR SEQ ID NO:374:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:374:

GGACUGCCGU CGCACC 16

(2) INFORMATION FOR SEQ ID NO:375:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:375:

CUGCCGUCGC ACCUCC 16

(2) INFORMATION FOR SEQ ID NO:376:

(i) SEQUENCE CHARACTERISTICS:
(A) LENGTH: 16 base pairs
(B) TYPE: nucleic acid ( C ) STRANDEDNESS: single
( D ) TOPOLOGY: linear ( x i ) SEQUENCE DESCRIPTION: SEQ ID NO:376:

GCACCGACUG AGCAAA 16

( 2 ) INFORMATION FOR SEQ ID NO:377:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:377:

UGGCAGCCCC UUAUUG 16

( 2 ) INFORMATION FOR SEQ ID NO:378:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:378:

UGGCAGCCCC UUAUUG 16

( 2 ) INFORMATION FOR SEQ ID NO:379:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:379:

CUGCAGUCGC ACCUCC 16

( 2 ) INFORMATION FOR SEQ ID NO:380:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:380:

GCACCGACUG AGCAAA 16

( 2 ) INFORMATION FOR SEQ ID NO:381:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:381:

UGGCAGCCCC UUAUUG 16

( 2 ) INFORMATION FOR SEQ ID NO:382:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:382:

GGACUGCCGU CGCACC 16

( 2 ) INFORMATION FOR SEQ ID NO:383:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:383:

CUGCCGUCGC ACCUCC 16

( 2 ) INFORMATION FOR SEQ ID NO:384:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:384:

CUACUGCCGA AAUCCA 16

( 2 ) INFORMATION FOR SEQ ID NO:385:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:385:

UGGCAGCCCC UUGGUG 16

( 2 ) INFORMATION FOR SEQ ID NO:386:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:386:

UGGCUGUUUC UGAACA 16

( 2 ) INFORMATION FOR SEQ ID NO:387:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:387:

AAACAGCCCU GGGGUC 16

( 2 ) INFORMATION FOR SEQ ID NO:388:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:388:

-continued

CCACUGUUGU UCCGGU                                                                16

( 2 ) INFORMATION FOR SEQ ID NO:389:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:389:

GUGCUGACUG CUGCUU                                                                16

( 2 ) INFORMATION FOR SEQ ID NO:390:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:390:

CUGCCGUCUC CAAAUU                                                                16

( 2 ) INFORMATION FOR SEQ ID NO:391:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:391:

UCACCGCCUG GACUGA                                                                16

( 2 ) INFORMATION FOR SEQ ID NO:392:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:392:

ACACUGUCCC CAGCUA                                                                16

RIBOZYMES TARGETED TO APO(A) RNA

This is a continuation of application Ser. No. 08/311,760 filed Sep. 23, 1994, now U.S. Pat. No. 5,599,706, hereby incorporated by reference in its totality (including drawings).

FIELD OF THE INVENTION

The present invention relates to therapeutic compositions and methods for the treatment or diagnosis of diseases or conditions related to Lp(a) levels, such as atherosclerosis, myocardial infarction, stroke, and restenosis.

BACKGROUND OF THE INVENTION

The following is a brief description of the physiological role of Lp(a). The discussion is not meant to be complete and is provided only for understanding of the invention that follows. This summary is not an admission that any of the work described below is prior art to the claimed invention.

Low density lipoproteins (LDL) are mainly composed of cholesterol, phospholipids and a single hydrophobic protein, apolipoprotein B [apoB]. They are considered as the major carriers of cholesterol in human plasma (for review see Uterman, G. (1989) *Science* 246, 904–910). ApoB, the only protein subunit of LDL, recognizes and binds to LDL receptors on the surface of cells. This LDL—LDL receptor interaction results in the internalization of the LDL and the eventual release of cholesterol inside the cell.

A modified form of LDL, termed as lipoprotein (a) [Lp(a)], was discovered in 1963 [Berg, K. (1963) *Acta Pathol. Microbiol. Scand.* 59, 369]. Covalent linkage of an additional glycoprotein, apo(a), to the LDL distinguishes Lp(a) from LDL. Several studies have recently suggested that elevated levels of Lp(a) in human plasma is linked to heart disease (Gurakar, et al., (1985) *Atherosclerosis* 57, 293–301; Leren, et al., (1988) *Atherosclerosis* 73, 135–141; Utermann, Supra). The Lp(a) levels range over 1000 fold and individuals with top quartile of plasma Lp(a) levels have two-to five-fold increased probability of developing atherosclerosis.

Atherosclerosis is a disease associated with hardening and loss of elasticity of arterial walls. High concentrations of cholesterol, in the form of Lp(a), in human blood plasma is one of the most important factors responsible for atherosclerosis. Deposition of cholesterol in the Macrophages and smooth muscle cells associated with arterial walls cause plaques (atheromatous lesions) which cause proliferation of adjoining smooth muscle cells. With time, these plaques grow in size causing hardening of the arterial walls and loss of elasticity, which in turn results in rupturing of the arterial walls, blood clotting and blockage of blood flow in the artery (for datails see *Textbook of medical physiology* Guyton, A. C., (Saunders Company, Philadelphia, 1991) pp. 761–764).

Lp(a) and/or apo(a) levels correlate well with an increased risk of atherosclerosis and its subsequent manifestations such as myocardial infarction, stroke, and restenosis. The apo(a) protein is unique to humans, Old World primates and hedgehogs; its absence in common laboratory animals has made exploration of the physiological role of apo(a) levels difficult. Recently, a transgenic mouse expressing the human gene encoding apo(a) was constructed [Lawn et al., (1992) *Nature* 360, 670–672]. The transgenic mice are more susceptible than control liter-mates to the development of lipid-rich regions in the aorta. Moreover, human apo(a) expression colocalizes to the regions of fat deposition. Thus, overexpression of apo(a) directly leads to atherosclerotic-like lesions in experimental animals. This observation lends credence to the hypothesis that elevated levels of apo(a) in humans contribute to atherosclerotic disease.

Apolipoprotein(a) is a large glycoprotein which varies in size from 300–800 KDa. Thirty four different isoforms have been characterized from human plasma. The only human cDNA clone currently available encompass 14 kilobase message that encodes apo(a) [McLean et al., (1987) *Nature* 330, 132–137]. A Rhesus monkey cDNA representing a part of the 3' end of the apo(a) mRNA has also been cloned and sequenced (Tomlinson et al., 1989 *J. Biol. Chem.* 264, 5957–5965). Sequence analysis of the cloned cDNA revealed two unique facets of the apo(a) structure. First, the apo(a) cDNA is remarkably repetitious. The reconstructed apo(a) cDNA encodes a protein of 4,529 amino acids; 4,210 of the residues are present in 37 repeats of 114 amino acids each. The repeated units themselves are especially homologous; 24 are identical in nucleotide sequence, four more share a sequence that differs in only three nucleotides and the remaining repeats differ by only 11 to 71 bases.

Secondly, apolipoprotein(a) is highly homologous to the serine protease, plasminogen. Plasminogen consists of five repeated homologous domains termed kringles (which are approximately 50% homologous in their amino sequences) followed by a trypsin-like protease domain. Kringle IV of plasminogen is very homologous to the 37 repeats of apo(a) [75–85% at the protein level). In addition, the 5' untranslated region, the signal peptide region, kringle V, the protease domain, and the 3' untranslated region of plasminogen are 98%, 100%, 91%, 94% and 87% homologous to apo(a) sequences, respectively. Relative to plasminogen, apo(a) is missing kringles I, II, and III and, as mentioned above, has extensively duplicated kringle IV. Despite the high degree of homology apo(a) cannot be converted into a protease by tissue type plasminogen activator (tPA). This is because of a single amino acid substitution in apo(a) at the site of activation of plasminogen by tPA (Utermann, supra). IN vitro studies have indicated that apo(a) and Lp(a) compete with plasminogen for binding to the plasminogen receptor and fibrin which supports the correlation between high Lp(a) levels and myocardial infraction (Gonzalez-Gronow et al., (1989) *Biochemistry* 28, 2374–2378; Hajjar et al., (1989) *Nature* 339, 303–305; Miles et al., (1989) *Nature* 339, 301–303). Recent in vivo studies in human (Moliterno et al., 1993 *Circulation* 88, 935–940) and monkey (Williams et al., 1993 *Atheroscler. Thromb.* 13, 548–554) support a role for Lp(a) in preventing clot lysis.

The extraordinary homology between apo(a) and plasminogen presents several barriers to drug development. Small molecule inhibitors of apo(a) would have to selectively bind apo(a) without negatively impacting plasminogen function. Similarly, antisense approaches will be limited by the overall nucleotide sequence homology between the two genes. Current dietary and drug therapies (Gurakar, et al., supra; Leren et al., supra), with the exception of nicotinic acid, have little or no effect on apo(a) levels.

Applicant now shows that these same limitations are opportunities for ribozyme therapy. The cleavage site specificity of ribozymes allows one to identify ribozyme target sites present in apo(a) mRNA but completely absent in the mRNA of plasminogen. For instance, there are 13 hammerhead cleavage sites present in the highly conserved kringles of apo(a) that are not present in kringle IV of plasminogen. Likewise, the last kringle repeat, protease domain and 3' untranslated region of apo(a) contain 21 hammerhead ribozyme cleavage sites present in apo(a) that are not present in plasminogen. Thus, ribozymes that target apo(a) mRNA represent unique therapeutics and diagnostic tools for the treatment and diagnosis of those at high risk of atherosclerosis.

SUMMARY OF THE INVENTION

This invention relates to ribozymes, or enzymatic RNA molecules, directed to cleave mRNA species encoding apo (a). In particular, applicant describes the selection and function of ribozymes capable of cleaving this RNA and their use to reduce levels of apo(a) in various tissues to treat the diseases discussed herein. Such ribozymes are also useful for diagnostic uses.

Ribozymes that cleave apo(a) mRNA represent a novel therapeutic approach to atherosclerosis. Ribozymes may show greater perdurance or lower effective doses than antisense molecules due to their catalytic properties and their inherent secondary and tertiary structures. Such ribozymes, with their catalytic activity and increased site specificity (as described below), represent more potent and safe therapeutic molecules than antisense oligonucleotides.

Applicant indicates that these ribozymes are able to inhibit expression of apo(a) and that the catalytic activity of the ribozymes is required for their inhibitory effect. Those of ordinary skill in the art, will find that it is clear from the examples described that other ribozymes that cleave target apo(a) encoding mRNAs may be readily designed and are within the invention.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its processing and translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf, T. M., et al., 1992, Proc. Natl. Acad. Sci. USA, 89, 7305–7309). Thus, the specificity of action of a ribozyme is greater than that of an antisense oligonucleotide binding the same RNA site.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, Aids Research and Human Retroviruses, 8, 183, of hairpin motifs by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, 1989, Biochemistry, 28, 4929, and Hampel et al., 1990, Nucleic Acids Res. 18,299, and an example of the hepatitis delta virus motif is described by Perrotta and Been, 1992, Biochemistry, 31, 16, of the RNaseP motif by Guerrier-Takada et al., 1983, Cell, 35, 849, Neurospora VS RNA ribozyme motif is described by Collins (Saville and Collins, 1990 Cell 61, 685–696; Saville and Collins, 1991 Proc. Natl. Acad. Sci. USA 88, 8826–8830; Collins and Olive, 1993 Biochemistry 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

The invention provides a method for producing a class of enzymatic cleaving agents which exhibit a high degree of specificity for the RNA of a desired target. The enzymatic nucleic acid molecule is preferably targeted to a highly conserved sequence region of a target apo(a) encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon, K. J., et al., 1991, Proc. Natl. Acad. Sci. USA, 88, 10591–5; Kashani-Sabet, M., et al., 1992, Antisense Res. Dev., 2, 3–15; Dropulic, B., et al., 1992, J Virol, 66,1432–41; Weerasinghe, M., et al., 1991, J Virol, 65, 5531–4; Ojwang, J. O., et al., 1992, Proc. Natl. Acad. Sci. USA, 89, 10802–6; Chen, C. J., et al., 1992, Nucleic Acids Res., 20, 4581–9; Sarver, H., et al., 1990, Science, 247, 1222–1225)). Those skilled in the art realize that any ribozyme can be expressed in eukaryotic cells from the appropriate DNA vector. The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa, J., et al., 1992, Nucleic Acids Symp. Ser., 27, 15–6; Taira, K., et al., 1991, Nucleic Acids Res., 19, 5125–30; Ventura, M., et al., 1993, Nucleic Acids Res., 21, 3249–55).

Thus, in a first aspect, the invention features ribozymes that inhibit apo(a) production. These chemically or enzymatically synthesized RNA molecules contain substrate binding domains that bind to accessible regions of their target mRNAs. The RNA molecules also contain domains that catalyze the cleavage of RNA. The RNA molecules are preferably ribozymes of the hammerhead or hairpin motif. Upon binding, the ribozymes cleave the target apo(a) encoding mRNAs, preventing translation and protein accumulation. In the absence of the expression of the target gene, a therapeutic effect may be observed.

By "inhibit" is meant that the activity or level of apo(a) encoding mRNA is reduced below that observed in the absense of the ribozyme, and preferably is below that level observed in the presence of an inactive RNA molecule able to bind to the same site on the mRNA, but unable to cleave that RNA.

Such ribozymes are useful for the prevention of the diseases and conditions discussed above, and any other diseases or conditions that are related to the level of apo(a) activity in a cell or tissue. By "related" is meant that the inhibition of apo(a) mRNA translation, and thus reduction in the level of apo(a), will relieve to some extent the symptoms of the disease or condition.

Ribozymes are added directly, or can be complexed with cationic lipids, packaged within liposomes, or otherwise delivered to target cells. The RNA or RNA complexes can be locally administered to relevant tissues through the use of a catheter, infusion pump or stent, with or without their incorporation in biopolymers. In preferred embodiments, the ribozymes have binding arms which are complementary to the sequences in Tables II, IV, VI and VII. Examples of such ribozymes are shown in Tables III, V, VI and VII Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit apo(a) activity are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids or adenovirus vectors. However, other mammalian cell vectors that direct the expression of RNA may be used for this purpose.

Other features and advantages of the invention will be apparent from the following description of the preferred embodiments thereof, and from the claims.

DESCRIPTION OF THE PREFFERED EMBODIMENTS

The drawings will first briefly be described.
Drawings:
FIG. 1 is a diagrammatic representation of the hammerhead ribozyme domain known in the art. Stem II can be ≧2 base-pair long or may be a loop region without base pairing.

Figure 2A:
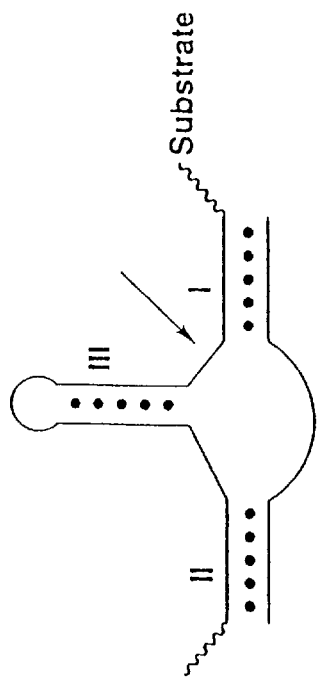
Figure 2B:
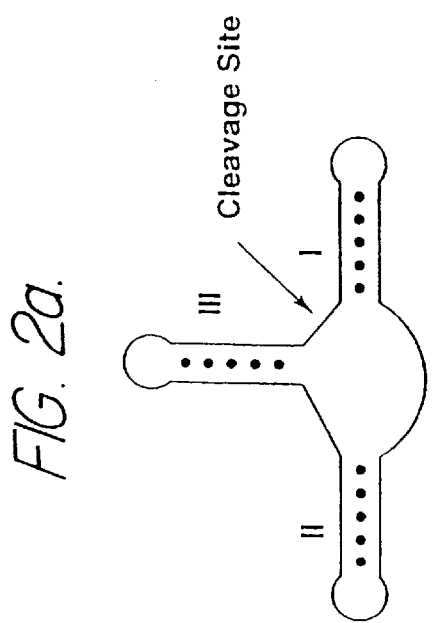
Figure 2C:
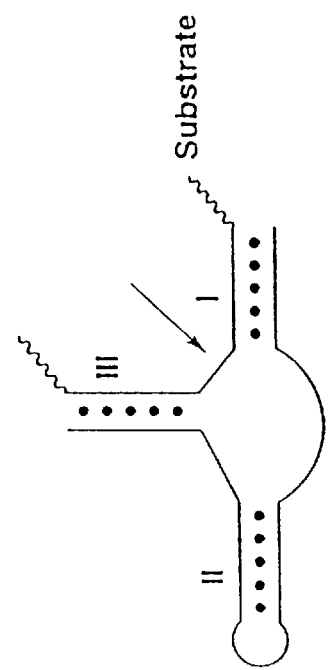
Figure 2D:
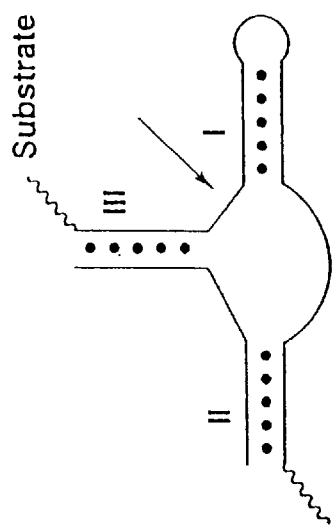

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

Figure 3:
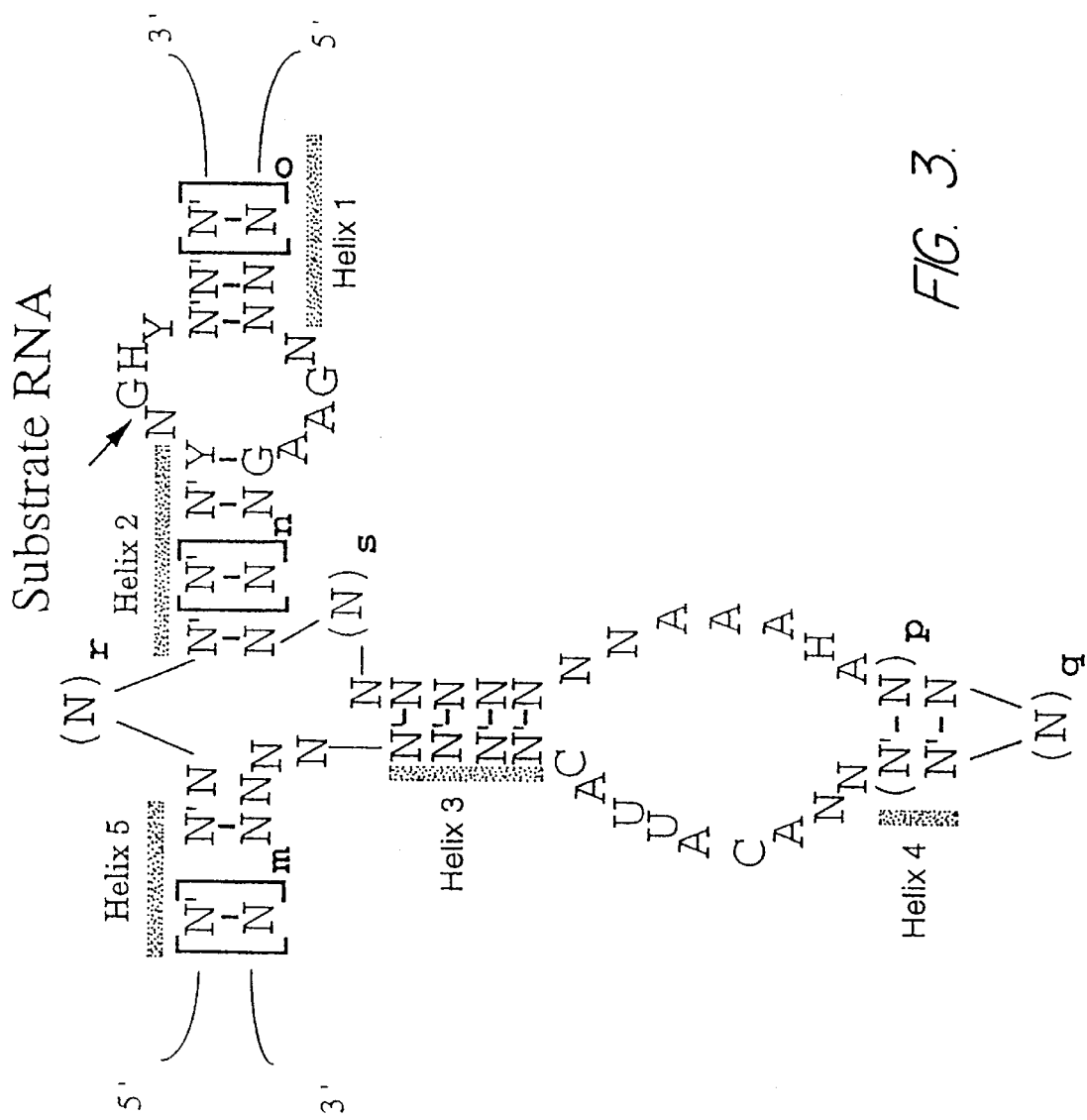
Figure 4:
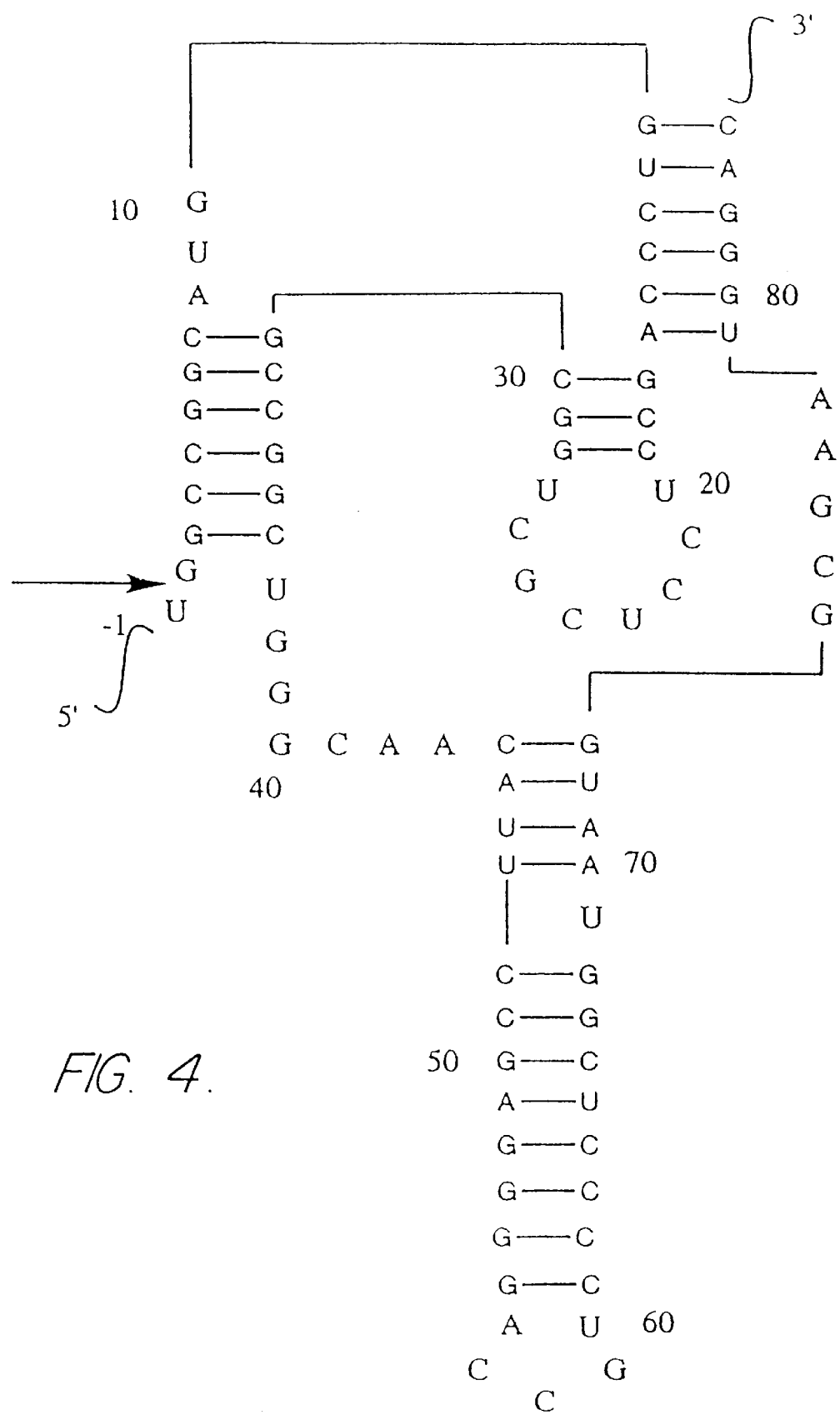

FIG. 3 is a representation of the general structure of the hairpin ribozyme domain known in the art. H, is A, U or C. Y is U or C. N is A, U, G, or C. N' is the complementary sequence of N. Helix 4 can be ≧2 base-pair long FIG. 4 is a representation of the general structure of the hepatitis delta virus ribozyme domain known in the art.

Figure 5:
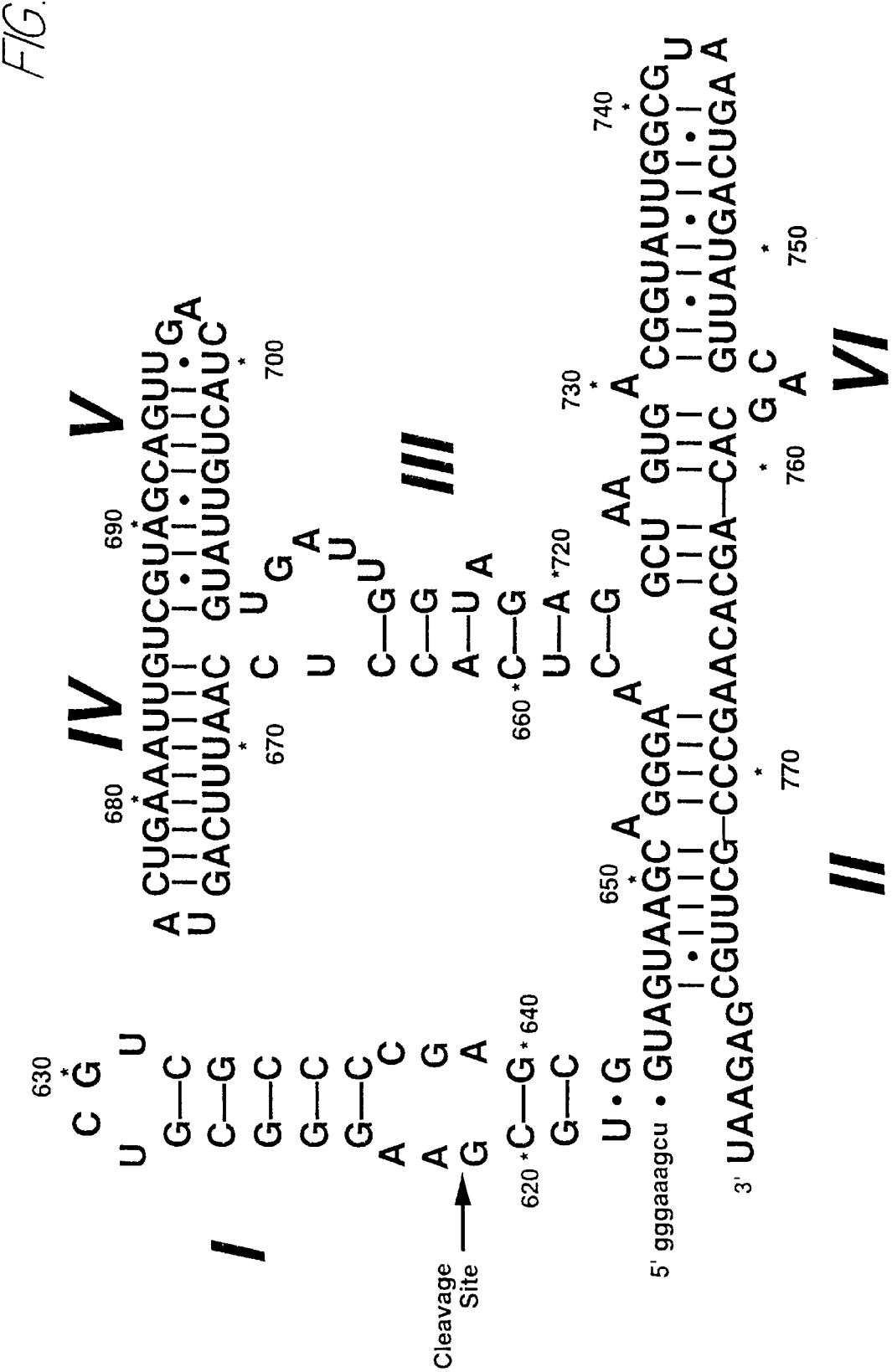

FIG. 5 is a representation of the general structure of the Neurospora VS RNA enzyme motif.

FIG. 6 is a schematic representation of an RNase H accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 5 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

Ribozymes

Ribozymes of this invention block to some extent apo(a) expression and can be used to treat disease or diagnose such disease. Ribozymes will be delivered to cells in culture and to tissues in animal models of Lp(a). Ribozyme cleavage of apo(a) mRNA in these systems may prevent or alleviate disease symptoms or conditions.

Target sites

Targets for useful ribozymes can be determined as disclosed in Draper et al supra, Sullivan et al., supra, as well as by Draper et al., "Method and reagent for treatment of arthritic conditions U.S. applications Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described. Such ribozymes can also be optimized and delivered as described therein. While specific examples to monkey and human RNA are provided, those in the art will recognize that the equivalent human RNA targets described can be used as described below. Thus, the same target may be used, but binding arms suitable for targetting human RNA sequences are present in the ribozyme. Such targets may also be selected as described below.

The sequence of human and monkey apo(a) mRNA can be screened for accessible sites using a computer folding algorithm. Regions of the mRNA that did not form secondary folding structures and that contain potential hammerhead or hairpin ribozyme cleavage sites can be identified. These sites are shown in Tables II, IV, and VI–VII. (All sequences are 5' to 3' in the tables.) While monkey and human sequences can be screened and ribozymes thereafter designed, the human targetted sequences are of most utility. However, as discussed in Stinchcomb et al. "Method and Composition for Treatment of Restenosis and Cancer Using Ribozymes," U.S. applications Ser. No. 08/245,466, filed May 18, 1994, and hereby incorporated by reference herein, monkey targeted ribozmes are useful to test efficacy of action of the ribozyme prior to testing in humans. The nucleotide base position is noted in the Tables as that site to be cleaved by the designated type of ribozyme.

Ribozyme target sites were chosen such that the cleavage sites are present in apo(a) mRNA but completely absent in the mRNA of plasminogen (Tables II, IV, VI and VII). This is because there exists extraordinary homology between apo(a) and plasminogen (see above).

It must be established that the sites predicted by the computer-based RNA folding algorithm correspond to potential cleavage sites. Hammerhead and hairpin ribozymes are designed that could bind and are individually analyzed by computer folding (Jaeger et al., 1989 *Proc. Natl. Acad. Sci. USA*, 86, 7706–7710) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA is screened for accessible cleavage sites by the method described generally in McSwiggen, U.S. patent application Ser. No. 07/883,849 filed May 1, 1992, entitled "Assay for ribozyme target site," hereby incorporated by reference herein. Briefly, DNA oligonucleotides representing potential hammerhead and hairpin ribozyme cleavage sites are synthesized. A polymerase chain reaction is used to generate a substrate for T7 RNA polymerase transcription from human or monkey apo(a) cDNA clones. Labeled RNA transcripts are synthesized in vitro from the two templates. The oligonucleotides and the labeled transcripts are annealed, RNaseH is added and the mixtures are incubated for the designated times at 37° C. Reactions are stopped and RNA separated on sequencing polyacrylamide gels. The percentage of the substrate cleaved is determined by autoradiographic quantitation using a phosphor imaging system. From these data, hammerhead or hairpin ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 *J. Am. Chem. Soc.*, 109, 7845–7854 and in Scaringe et al., 1990 *Nucleic Acids Res.*, 18, 5433–5441 and makes use of common nucleic acid protecting and coupling groups, such as dimethoxytrityl at the 5'-end, and phosphoramidites at the 3'-end. The average stepwise coupling yields were >98%. Inactive ribozymes are synthesized by substituting a U for $G_5$ and a U for $A_{14}$ (numbering from Hertel et al., 1992 *Nucleic Acids Res.*, 20, 3252). Hairpin ribozymes are synthesized in two parts and annealed to reconstruct the active ribozyme (Chowrira and Burke, 1992 *Nucleic Acids Res.*, 20, 2835–2840). All ribozymes are modified to enhance stability by modification of five ribonucleotides at both the 5' and 3' ends with 2'-O-methyl groups. Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. applications Ser. No. 08/245,736, the totality of which is hereby incorporated herein by reference.) and were resuspended in water.

The sequences of the chemically synthesized ribozymes useful in this study are shown in Tables II, V, VI, and VII. Those in the art will recognize that these sequences are representative only of many more such sequences where the enzymatic portion of the ribozyme (all but the binding arms) is altered to affect activity. For example, stem loop II sequence of hammerhead ribozymes listed in Tables III and V (5'-GGCCGAAAGGCC-3') can be altered (substitution, deletion and/or insertion) to contain any sequence provided a minimum of two base-paired stem structure can form. Similarly, stem-loop IV sequence of hairpin ribozymes listed in Tables VI and VII (5'-CACGUUGUG-3') can be altered (substitution, deletion and/or insertion) to contain any sequence provided, a minimum of two base-paired stem structure can form. The sequences listed in Tables III, V–VII may be formed of ribonucleotides or other nucleotides or non-nucleotides. Such ribozymes are equivalent to the ribozymes described specifically in the Tables.

Optimizing Ribozyme Activity Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman,N. et al. U.S. patent application Ser. No. 07/829,729, and Sproat, European Patent Application 92110298.4 and U.S. Pat. No. 5,334,711 and Jennings et al., WO 94/13688, which describe various chemical modifications that can be made to the sugar moieties of enzymatic RNA molecules. All these publications are hereby incorporated by reference herein.), modifications which enhance their efficacy in cells, and removal of stem II bases to shorten RNA synthesis times and reduce chemical requirements.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. The RNA/vehicle combination is locally delivered by direct injection or by use of a catheter, infusion pump or stent. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.* 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Liszięwicz et al., 1993 *Proc. Natl. Acad. Sci. U.S.A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral, Sindbis virus, Semliki forest virus vectors).

In a preferred embodiment of the invention, a transcription unit expressing a ribozyme that cleaves apo(a) RNA is inserted into a plasmid DNA vector, a retrovirus DNA viral vector, an adenovirus DNA viral vector or an adeno-associated virus vector. These and other vectors have been used to transfer genes to live animals (for a review see Friedman, 1989 *Science* 244, 1275–1281; Roemer and Friedman, 1992 *Eur. J. Biochem.* 208, 211–225) and leads to transient or stable gene expression. The vectors are delivered as recombinant viral particles. DNA may be delivered alone or complexed with vehicles (as described for RNA above). The DNA, DNA/vehicle complexes, or the recombinant virus particles are locally administered to the site of treatment, e.g., through the use of a catheter, stent or infusion pump.

Example 1: apo(a) Hammerhead ribozymes

By engineering ribozyme motifs we have designed several ribozymes directed against apo(a) mRNA sequences. These have been synthesized with modifications that improve their nuclease resistance. These ribozymes cleave apo(a) target sequences in vitro.

The ribozymes will be tested for function in vivo by exogenous delivery to cells expressing apo(a). Ribozymes are delivered by incorporation into liposomes, by complexing with cationic lipids, by microinjection, or by expression from DNA vectors. Expression of apo(a) is monitored by ELISA, by indirect immunofluoresence, and/or by FACS analysis. Levels of apo(a) mRNA are assessed by Northern analysis, RNase protection, by primer extension analysis or by quantitative RT-PCR techniques. Ribozymes that block the induction of apo(a) protein and mRNA by more than 90% are identified.

Diagnostic uses

Ribozymes of this invention may be used as diagnostic tools to examine genetic drift and mutations within diseased cells. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an apo(a) related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., apo(a)) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns
Size: ~200 to >1000 nucleotides.
Requires a U in the target sequence immediately 5' of the cleavage site.
Binds 4–6 nucleotides at 5' side of cleavage site.
Over 75 known members of this class. Found in Tetrahymena thermophila rRNA, fungal mitochondria, chloroplasts, phage T4, blue-green algae, and others.
RNAseP RNA (M1 RNA)
Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead Ribozyme
Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIGS. 1 and 2)
Hairpin Ribozyme
Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme
Size: 50–60 nucleotides (at present).
Cleavage of target RNAs recently demonstrated.
Sequence requirements not fully determined.
Binding sites and structural requirements not fully determined, although no sequences 5' of cleavage site are required.

Only 1 known member of this class. Found in human HDV (FIG. 4)

Neurospora VS RNA Ribozyme
Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Unique Human apo(a) HH Target sequence

| nt | HH Target Sequence | SEQ ID NO. | nt | HH Target Sequence | SEQ ID NO. |
|---|---|---|---|---|---|
| 127 | CCAGGAU U GCUACCA | 7 | 11186 | ACAGAAU A UUAUCCA | 47 |
| 151 | ACAGAGU U AUCGAGG | 8 | 11254 | UUGGUGU U AUACCAU | 48 |
| 154 | GAGUUAU C GAGGCAC | 9 | 11257 | GUGUUAU A CCAUGGA | 49 |
| 199 | CCAAGCU U GGUCAUC | 10 | 11266 | CAUGGAU C CCAAUGU | 50 |
| 362 | CAAUGCU C AGACGCA | 11 | 11305 | ACAAUGU C CAGUGAC | 51 |
| 400 | GACUGUU A CCCCGGU | 12 | 11347 | GGCUGUU U CUGAACA | 52 |
| 408 | CCCCGGU U CCAAGCC | 13 | 11348 | GCUGUUU C UGAACAA | 53 |
| 409 | CCCGGUU C CAAGCCU | 14 | 11423 | CGAGGCU C AUUCUCC | 54 |
| 417 | CAAGCCU A GAGGCUC | 15 | 11427 | GCUCAUU C UCCACCA | 55 |
| 481 | CCAUGGU A AUGGACA | 16 | 11429 | UCAUUCU C CACCACU | 56 |
| 571 | GCAUAGU C GGACCCC | 17 | 11440 | CACUGUU A CAGGAAG | 57 |
| 9031 | CCACGGU A AUGGACA | 18 | 11653 | CACAACU C CCACGGU | 58 |
| 10207 | UCCAGAU C CUGUGGC | 19 | 11670 | UCCCAGU U CCAAGCA | 59 |
| 10222 | AGCCCCU U AUUGUUA | 20 | 11779 | CACCACU A UCACAGG | 60 |
| 10223 | GCCCCUU A UUGUUAU | 21 | 11797 | AACAUGU C AGUCUUG | 61 |
| 10225 | CCCUUAU U GUUAUAC | 22 | 11824 | ACCACAU U GGCAUCG | 62 |
| 10345 | GGCUCCU U CUGAACA | 23 | 11988 | GUGUCCU C ACAACUC | 63 |
| 10346 | GCUCCUU C UGAACAA | 24 | 12013 | CCCGGUU C CAAGCAC | 64 |
| 10532 | AAGAACU A CUGCCGA | 25 | 12159 | CUAUGAU A CCACACU | 65 |
| 10543 | CCGAAAU C CAGAUCC | 26 | 12235 | UCCAGAU U CUGGGAA | 66 |
| 10564 | AGCCCCU U GGUGUUA | 27 | 12236 | CCAGAUU C UGGGAAA | 67 |
| 10570 | UUGGUGU U AUACAAC | 28 | 12320 | ACAGAAU C AGGUGUC | 68 |
| 10622 | CGAUGCU C AGAUGCA | 29 | 12327 | CAGGUGU C CUAGAGA | 69 |
| 10677 | CAAGCCU A GAGGCUU | 30 | 12330 | GUGUCCU A GAGACUC | 70 |
| 10687 | GGCUUUU U UUGAACA | 31 | 12337 | AGAGACU C CCACUGU | 71 |
| 10736 | UGCUACU A CCAUUAU | 32 | 12374 | GCUCAUU C UGAAGCA | 72 |
| 10741 | CUACCAU U AUGGACA | 33 | 12453 | GCACAUU C UCCACCA | 73 |
| 10742 | UACCAUU A UGGACAG | 34 | 12481 | GACAUGU C AAUCUUG | 74 |
| 10792 | AAGAACU U GCCAAGC | 35 | 12592 | AGGCCCU U GGUGUUU | 75 |
| 10828 | CCAGCAU A GUCGGAC | 36 | 12650 | CGAUGCU C AGACACA | 76 |
| 10899 | CUGAGAU U CGCCCUU | 37 | 12974 | GCAUCCU C UUCAUUU | 77 |
| 10900 | UGAGAUU C GCCCUUG | 38 | 12976 | AUCCUCU U CAUUUGA | 78 |
| 10906 | UCGCCCU U GGUGUUA | 39 | 13119 | GCACCUU A AUAUCCC | 79 |
| 10924 | CAUGGAU C CCAGUGU | 40 | 13226 | CUCGAAU C UCAUGUU | 80 |
| 10976 | ACAGAAU C AAGUGUC | 41 | 13228 | CGAAUCU C AUGUUCA | 81 |
| 10983 | CAAGUGU C CUUGCAA | 42 | 13839 | UGGUAUU U UUGUGUA | 82 |
| 10986 | GUGUCCU U GCAACUC | 43 | 13848 | UGUGUAU A AGCUUUU | 83 |
| 11011 | CCCAGAU C CAAGCAC | 44 | 13930 | ACUUAUU U UGAUUUG | 84 |
| 11098 | GAGUUAU C GAGGCUC | 45 | 13931 | CUUAUUU U GAUUUGA | 85 |
| 11170 | CUGGCAU C AGAGGAC | 46 | | | |

TABLE III

Unique Human apo(a) HH Ribozyme Sequence

| nt. position | Human apo (a) HH Ribozyme Sequence | SEQ ID NO. |
|---|---|---|
| 127 | UGGUAGC CUGAUGAGGCCGAAAGGCCGAA AUCCUGG | 86 |
| 151 | CCUCGAU CUGAUGAGGCCGAAAGGCCGAA ACUCUGU | 87 |
| 154 | GUGCCUC CUGAUGAGGCCGAAAGGCCGAA AUAACUC | 88 |
| 199 | GAUGACC CUGAUGAGGCCGAAAGGCCGAA AGCUUGG | 89 |
| 362 | UGCGUCU CUGAUGAGGCCGAAAGGCCGAA AGCAUUG | 90 |
| 400 | ACCGGGG CUGAUGAGGCCGAAAGGCCGAA AACAGUC | 91 |
| 408 | GGCUUGG CUGAUGAGGCCGAAAGGCCGAA ACCGGGG | 92 |
| 409 | AGGCUUG CUGAUGAGGCCGAAAGGCCGAA AACCGGG | 93 |
| 417 | GAGCCUC CUGAUGAGGCCGAAAGGCCGAA AGGCUUG | 94 |
| 481 | UGUCCAU CUGAUGAGGCCGAAAGGCCGAA ACCAUGG | 95 |
| 571 | GGGGUCC CUGAUGAGGCCGAAAGGCCGAA ACUAUGC | 96 |

TABLE III-continued

Unique Human apo(a) HH Ribozyme Sequence

| nt. position | Human apo (a) HH Ribozyme Sequence | SEQ ID NO. |
|---|---|---|
| 9031 | UGUCCAU CUGAUGAGGCCGAAAGGCCGAA ACCGUGG | 97 |
| 10207 | GCCACAG CUGAUGAGGCCGAAAGGCCGAA AUCUGGA | 98 |
| 10222 | UAACAAU CUGAUGAGGCCGAAAGGCCGAA AGGGGCU | 99 |
| 10223 | AUAACAA CUGAUGAGGCCGAAAGGCCGAA AAGGGGC | 100 |
| 10225 | GUAUAAC CUGAUGAGGCCGAAAGGCCGAA AUAAGGG | 101 |
| 10345 | UGUUCAG CUGAUGAGGCCGAAAGGCCGAA AGGAGCC | 102 |
| 10346 | UUGUUCA CUGAUGAGGCCGAAAGGCCGAA AAGGAGC | 103 |
| 10532 | UCGGCAG CUGAUGAGGCCGAAAGGCCGAA AGUUCUU | 104 |
| 10543 | GGAUCUG CUGAUGAGGCCGAAAGGCCGAA AUUUCGG | 105 |
| 10564 | UAACACC CUGAUGAGGCCGAAAGGCCGAA AGGGGCU | 106 |
| 10570 | GUUGUAU CUGAUGAGGCCGAAAGGCCGAA ACACCAA | 107 |
| 10622 | UGCAUCU CUGAUGAGGCCGAAAGGCCGAA AGCAUCG | 108 |
| 10677 | AAGCCUC CUGAUGAGGCCGAAAGGCCGAA AGGCUUG | 109 |
| 10687 | UGUUCAA CUGAUGAGGCCGAAAGGCCGAA AAAAGCC | 11o |
| 10736 | AUAAUGG CUGAUGAGGCCGAAAGGCCGAA AGUAGCA | 111 |
| 10741 | UGUCCAU CUGAUGAGGCCGAAAGGCCGAA AUGGUAG | 112 |
| 10742 | CUGUCCA CUGAUGAGGCCGAAAGGCCGAA AAUGGUA | 113 |
| 10792 | GCUUGGC CUGAUGAGGCCGAAAGGCCGAA AGUUCUU | 114 |
| 10828 | GUCCGAC CUGAUGAGGCCGAAAGGCCGAA AUGCUGG | 115 |
| 10899 | AAGGGCG CUGAUGAGGCCGAAAGGCCGAA AUCUCAG | 116 |
| 10900 | CAAGGGC CUGAUGAGGCCGAAAGGCCGAA AAUCUCA | 117 |
| 10906 | UAACACC CUGAUGAGGCCGAAAGGCCGAA AGGGCGA | 118 |
| 10924 | ACACUGG CUGAUGAGGCCGAAAGGCCGAA AUCCAUG | 119 |
| 10976 | GACACUU CUGAUGAGGCCGAAAGGCCGAA AUUCUGU | 120 |
| 10983 | UUGCAAG CUGAUGAGGCCGAAAGGCCGAA ACACUUG | 121 |
| 10986 | GAGUUGC CUGAUGAGGCCGAAAGGCCGAA AGGACAC | 122 |
| 11011 | GUGCUUG CUGAUGAGGCCGAAAGGCCGAA AUCUGGG | 123 |
| 11098 | GAGCCUC CUGAUGAGGCCGAAAGGCCGAA AUAACUC | 124 |
| 11170 | GUCCUCU CUGAUGAGGCCGAAAGGCCGAA AUGCCAG | 125 |
| 11186 | UGGAUAA CUGAUGAGGCCGAAAGGCCGAA AUUCUGU | 126 |
| 11254 | AUGGUAU CUGAUGAGGCCGAAAGGCCGAA ACACCAA | 127 |
| 11257 | UCCAUGG CUGAUGAGGCCGAAAGGCCGAA AUAACAC | 128 |
| 11266 | ACAUUGG CUGAUGAGGCCGAAAGGCCGAA AUCCAUG | 129 |
| 11305 | GUCACUG CUGAUGAGGCCGAAAGGCCGAA ACAUUGU | 130 |
| 11347 | UGUUCAG CUGAUGAGGCCGAAAGGCCGAA AACAGCC | 131 |
| 11348 | UUGUUCA CUGAUGAGGCCGAAAGGCCGAA AAACAGC | 132 |
| 11423 | GGAGAAU CUGAUGAGGCCGAAAGGCCGAA AGCCUCG | 133 |
| 11427 | UGGUGGA CUGAUGAGGCCGAAAGGCCGAA AAUGAGC | 134 |
| 11429 | AGUGGUG CUGAUGAGGCCGAAAGGCCGAA AGAAUGA | 135 |
| 11440 | CUUCCUG CUGAUGAGGCCGAAAGGCCGAA AACAGUG | 136 |
| 11653 | ACCGUGG CUGAUGAGGCCGAAAGGCCGAA AGUUGUG | 137 |
| 11670 | UGCUUGG CUGAUGAGGCCGAAAGGCCGAA ACUGGGA | 138 |
| 11779 | CCUGUGA CUGAUGAGGCCGAAAGGCCGAA AGUGGUG | 139 |
| 11797 | CAAGACU GUGAUGAGGCCGAAAGGCCGAA ACAUGUU | 140 |
| 11B24 | CGAUGCC CUGAUGAGGCCGAAAGGCCGAA AUGUGGU | 141 |
| 11988 | GAGUUGU CUGAUGAGGCCGAAAGGCCGAA AGGACAC | 142 |
| 12013 | GUGCUUG CUGAUGAGGCCGAAAGGCCGAA AACCGGG | 143 |
| 12159 | AGUGUGG CUGAUGAGGCCGAAAGGCCGAA AUCAUAG | 144 |
| 12235 | UUCCCAG CUGAUGAGGCCGAAAGGCCGAA AUCUGGA | 145 |
| 12236 | UUUCCCA CUGAUGAGGCCGAAAGGCCGAA AAUCUGG | 146 |
| 12320 | GACACCU CUGAUGAGGCCGAAAGGCCGAA AUUCUGU | 147 |
| 12327 | UCUCUAG CUGAUGAGGCCGAAAGGCCGAA ACACCUG | 148 |
| 12330 | GAGUCUC CUGAUGAGGCCGAAAGGCCGAA AGGACAC | 149 |
| 12337 | ACAGUGG CUGAUGAGGCCGAAAGGCCGAA AGUCUCU | 150 |
| 12374 | UGCUUCA CUGAUGAGGCCGAAAGGCCGAA AAUGAGC | 151 |
| 12453 | UGGUGGA CUGAUGAGGCCGAAAGGCCGAA AAUGUGC | 152 |
| 12481 | CAAGAUU CUGAUGAGGCCGAAAGGCCGAA ACAUGUC | 153 |
| 12592 | AAACACC CUGAUGAGGCCGAAAGGCCGAA AGGGCCU | 154 |
| 12650 | UGUGUCU CUGAUGAGGCCGAAAGGCCGAA AGCAUCG | 155 |
| 12974 | AAAUGAA CUGAUGAGGCCGAAAGGCCGAA AGGAUGC | 156 |
| 12976 | UCAAAUG CUGAUGAGGCCGAAAGGCCGAA AGAGGAU | 157 |
| 13119 | GGGAUAU CUGAUGAGGCCGAAAGGCCGAA AAGGUGC | 158 |
| 13226 | AACAUGA CUGAUGAGGCCGAAAGGCCGAA AUUCGAG | 159 |
| 13228 | UGAACAU CUGAUGAGGCCGAAAGGCCGAA AGAUUCG | 160 |
| 13839 | UACACAA CUGAUGAGGCCGAAAGGCCGAA AAUACCA | 161 |
| 13848 | AAAAGCU CUGAUGAGGCCGAAAGGCCGAA AUACACA | 162 |
| 13930 | CAAAUCA CUGAUGAGGCCGAAAGGCCGAA AAUAAGU | 163 |
| 13931 | UCAAAUC CUGAUGAGGCCGAAAGGCCGAA AAAUAAG | 164 |

TABLE IV

Unique Monkey apo(a) HH Target sequence

| nt. | HH Target Sequence | SEQ ID NO. | nt. | HH Target Sequence | SEQ ID NO. |
|---|---|---|---|---|---|
| 127 | CUGCCGU C GCaCCUC | 165 | 11170 | ACAaUgU C UGGUgAC | 204 |
| 151 | CUGCCGU C GCaCCUC | 166 | 11186 | ACAGAAU C AAGUGUC | 205 |
| 154 | CUGCCgU C GCaCCUC | 167 | 11254 | gCUUcUU c UgaAGAA | 206 |
| 199 | CCCCGGU U CCAAGCC | 168 | 11257 | GACUGCU A CCAUGGU | 207 |
| 362 | AGAGGCU C CUUCCGA | 169 | 11266 | GAGUUAU C GAGGCUC | 208 |
| 400 | GGCUCCU U CCGAACA | 170 | 11305 | CGAGGCU C AUUCUCC | 209 |
| 408 | GGCUCCU U CCGAACA | 171 | 11347 | UCAUUCU C CACCACU | 210 |
| 409 | GGCUCCU U CCGAACA | 172 | 11348 | GACAUGU C AGUCUUG | 211 |
| 417 | GGCUCCU U CCGAACA | 173 | 11423 | UCUUGGU C CUCUAUG | 212 |
| 481 | GCUCCUU C CGAACAA | 174 | 11427 | UGGUCCU C UAUGACA | 213 |
| 571 | ACAGAGU U AUCGAGG | 175 | 11429 | UGGUCCU C UAUGACA | 214 |
| 9031 | GAGUUAU C GAGGCAC | 176 | 11440 | GUCCUCU A UGACACC | 215 |
| 10207 | CCACACU C UCAUAGU | 177 | 11653 | auAGAAU A CUACCCA | 216 |
| 10222 | CCACACU C uCAUAGU | 178 | 11670 | auAGAAU A CUACCCA | 217 |
| 10223 | AGAGGCU C CUUCUGA | 179 | 11779 | aUGgAaU c AaGUGUC | 218 |
| 10225 | AGAGGCU c CUUCUGA | 180 | 11797 | CAAGUGU C CUUGCaA | 219 |
| 10345 | GUGUUAU A CAACgGA | 181 | 11824 | UCCCAGU U CCAAGCA | 220 |
| 10346 | AACgGAU C CCAGUGU | 182 | 11988 | UCGGCAU C GGAGGAU | 221 |
| 10532 | AGaGGcU u UUCUuga | 183 | 12013 | UCCCAUU A cgCUAUC | 222 |
| 10543 | AGAGGCU U UUcUUGA | 184 | 12159 | GCUCCUU C UGAACAA | 223 |
| 10564 | GAGGCuU u UCuUgaA | 185 | 12235 | CCAGGAU U GCUACCA | 224 |
| 10570 | AGGCUUU U cUUGAAC | 186 | 12236 | CCAGGAU U GCUACCA | 225 |
| 10622 | UgCUACU a CcaUUAU | 187 | 12320 | gaACUGU c aGUcUuG | 226 |
| 10677 | GGCACAU A CUCCACC | 188 | 12327 | UCUUGGU C AUCUAUG | 227 |
| 10687 | CCACUGU u ACAGGAA | 189 | 12330 | UGGUCAU C UAUGAUA | 228 |
| 10736 | ccACUGU u ACAGGAA | 190 | 12337 | GUCAUCU A UGAUACC | 229 |
| 10141 | CCACUGU u ACAGGAA | 191 | 12374 | UGGUGUU A CACgACU | 230 |
| 10742 | CCACUGU u ACAGGAA | 192 | 12453 | AgagaCU c CCACUGU | 231 |
| 10792 | CACUGUU A CaGGaAg | 193 | 12481 | CUGUUGU U CCgGUUC | 232 |
| 10828 | GCAUAGU C GGACCCC | 194 | 12592 | GCUCAUU C UGAAGCA | 233 |
| 10899 | GCAUAGU C GGACCCC | 195 | 12650 | UCAAUCU U GGUCAUC | 234 |
| 10900 | GCAUAGU C GGACCCC | 196 | 12974 | CCACAUU C CUGGCCC | 235 |
| 10906 | AaAaACU a UCcaaAu | 197 | 12976 | GGCAAGU C AGUCUuA | 236 |
| 10924 | CAGGAAU C CAGAUGC | 198 | 13119 | AgGccuu c CUUCUAC | 237 |
| 10976 | CAGGAAU C CAGAUGC | 199 | 13226 | AGUGUCU A GGuUGUU | 238 |
| 10983 | CAGGAAU C CAGAUGC | 200 | 13228 | aGuGUCU a GGuUGUu | 239 |
| 10986 | CAGGAAU C CAGAUGC | 201 | 13839 | UGGUAUU a UUGUGUA | 240 |
| 11011 | CAGGAAU C CAGAUGC | 202 | 13848 | UAAGCUU U UcccGUC | 241 |
| 11098 | UcGcCCU U GGUGUUA | 203 | | | |

TABLE V

Unique Monkey apo(a) HH Ribozyme Sequence

| nt. | Monkey apo (a) HH Ribozyme Sequence | SEQ ID NO. |
|---|---|---|
| 127 | GAGGUGC CUGAUGAGGCCGAAAGGCCGAA ACGGCAG | 242 |
| 151 | GAGGUGC CUGAUGAGGCCGAAAGGCCGAA ACGGCAG | 243 |
| 154 | GAGGUGC CUGAUGAGGCCGAAAGGCCGAA ACGGCAG | 244 |
| 199 | GGCUUGG CUGAUGAGGCCGAAAGGCCGAA ACCGGGG | 245 |
| 362 | UCGGAAG CUGAUGAGGCCGAAAGGCCGAA AGCCUCU | 246 |
| 400 | UGUUCGG CUGAUGAGGCCGAAAGGCCGAA AGGAGCC | 247 |
| 408 | UGUUCGG CUGAUGAGGCCGAAAGGCCGAA AGGAGCC | 248 |
| 409 | UGUUCGG CUGAUGAGGCCGAAAGGCCGAA AGGAGCC | 249 |
| 417 | UGUUCGG CUGAUGAGGCCGAAAGGCCGAA AGGAGCC | 250 |
| 481 | UUGUUCG CUGAUGAGGCCGAAAGGCCGAA AAGGAGC | 251 |
| 571 | CCUCGAU CUGAUGAGGCCGAAAGGCCGAA ACUCUGU | 252 |
| 9031 | CUGCCUC CUGAUGAGGCCGAAAGGCCGAA AUAACUC | 253 |
| 10207 | ACUAUGA CUGAUGAGGCCGAAAGGCCGAA AGUGUGG | 254 |
| 10222 | ACUAUGA CUGAUGAGGCCGAAAGGCCGAA AGUGUGG | 255 |
| 10223 | UCAGAAG CUGAUGAGGCCGAAAGGCCGAA AGCCUCU | 256 |
| 10225 | UCAGAAG CUGAUGAGGCCGAAAGGCCGAA AGCCUCU | 257 |
| 10345 | UCCGUUG CUGAUGAGGCCGAAAGGCCGAA AUAACAC | 258 |
| 10346 | ACACUGG CUGAUGAGGCCGAAAGGCCGAA AUCCGUU | 259 |
| 10532 | UCAAGAA CUGAUGAGGCCGAAAGGCCGAA AGCCUCU | 260 |
| 10543 | UCAAGAA CUGAUGAGGCCGAAAGGCCGAA AGCCUCU | 261 |
| 10564 | UUCAAGA CUGAUGAGGCCGAAAGGCCGAA AAGCCUC | 262 |
| 10570 | GUUCAAG CUGAUGAGGCCGAAAGGCCGAA AAAGCCU | 263 |
| 10622 | AUAAUGG CUGAUGAGGCCGAAAGGCCGAA AGUAGCA | 264 |
| 10677 | GGUGGAG CUGAUGAGGCCGAAAGGCCGAA AUGUGCC | 265 |
| 10687 | UUCCUGU CUGAUGAGGCCGAAAGGCCGAA ACAGUGG | 266 |

TABLE V-continued

Unique Monkey apo(a) HH Ribozyme Sequence

| nt. | Monkey apo (a) HH Ribozyme Sequence | SEQ ID NO. |
|---|---|---|
| 10736 | UUCCUGU CUGAUGAGGCCGAAAGGCCGAA ACAGUGG | 267 |
| 10741 | UUCCUGU CUGAUGAGGCCGAAAGGCCGAA ACAGUGG | 268 |
| 10742 | UUCCUGU CUGAUGAGGCCGAAAGGCCGAA ACAGUGG | 269 |
| 10792 | CUUCCUG CUGAUGAGGCCGAAAGGCCGAA AACAGUG | 270 |
| 10828 | GGGGUCC CUGAUGAGGCCGAAAGGCCGAA ACUAUGC | 271 |
| 10899 | GGGGUCC CUGAUGAGGCCGAAAGGCCGAA ACUAUGC | 272 |
| 10900 | GGGGUCC CUGAUGAGGCCGAAAGGCCGAA ACUAUGC | 273 |
| 10906 | AUUUGGA CUGAUGAGGCCGAAAGGCCGAA AGUUUUU | 274 |
| 10924 | GCAUCUG CUGAUGAGGCCGAAAGGCCGAA AUUCCUG | 275 |
| 10976 | GCAUCUG CUGAUGAGGCCGAAAGGCCGAA AUUCCUG | 276 |
| 10983 | GCAUCUG CUGAUGAGGCCGAAAGGCCGAA AUUCCUG | 277 |
| 10985 | GCAUCUG CUGAUGAGGCCGAAAGGCCGAA AUUCCUG | 278 |
| 11011 | GCAUCUG CUGAUGAGGCCGAAAGGCCGAA AUUCCUG | 279 |
| 11098 | UAACACC CUGAUGAGGCCGAAAGGCCGAA AGGGCGA | 280 |
| 11170 | GUCACCA CUGAUGAGGCCGAAAGGCCGAA ACAUUGU | 281 |
| 11186 | GACACUU CUGAUGAGGCCGAAAGGCCGAA AUUCUGU | 282 |
| 11254 | UUCUUCA CUGAUGAGGCCGAAAGGCCGAA AAGAAGC | 283 |
| 11257 | ACCAUGG CUGAUGAGGCCGAAAGGCCGAA AGCAGUC | 284 |
| 11266 | GAGCCUC CUGAUGAGGCCGAAAGGCCGAA AUAACUC | 285 |
| 11305 | GGAGAAU CUGAUGAGGCCGAAAGGCCGAA AGCCUCG | 286 |
| 11347 | AGUGGUG CUGAUGAGGCCGAAAGGCCGAA AGAAUGA | 287 |
| 11348 | CAAGACU CUGAUGAGGCCGAAAGGCCGAA ACAUGUC | 288 |
| 11423 | CAUAGAG CUGAUGAGGCCGAAAGGCCGAA ACCAAGA | 289 |
| 11427 | UGUCAUA CUGAUGAGGCCGAAAGGCCGAA AGGACCA | 290 |
| 11429 | UGUCAUA CUGAUGAGGCCGAAAGGCCGAA AGGACCA | 291 |
| 11440 | GGUGUCA CUGAUGAGGCCGAAAGGCCGAA AGAGGAC | 292 |
| 11653 | UGGGUAG CUGAUGAGGCCGAAAGGCCGAA AUUCUAU | 293 |
| 11670 | UGGGUAG CUGAUGAGGCCGAAAGGCCGAA AUUCUAU | 294 |
| 11779 | GACACUU CUGAUGAGGCCGAAAGGCCGAA AUUCCAU | 295 |
| 11797 | UUGCAAG CUGAUGAGGCCGAAAGGCCGAA ACACUUG | 296 |
| 11824 | UGCUUGG CUGAUGAGGCCGAAAGGCCGAA ACUGGGA | 297 |
| 11988 | AUCCUCC CUGAUGAGGCCGAAAGGCCGAA AUGCCGA | 298 |
| 12013 | GAUAGCG CUGAUGAGGCCGAAAGGCCGAA AAUGGGA | 299 |
| 12159 | UUGUUCA CUGAUGAGGCCGAAAGGCCGAA AAGGAGC | 300 |
| 12235 | UGGUAGC CUGAUGAGGCCGAAAGGCCGAA AUCCUGG | 301 |
| 12236 | UGGUAGC CUGAUGAGGCCGAAAGGCCGAA AUCCUGG | 302 |
| 12320 | CAAGACU CUGAUGAGGCCGAAAGGCCGAA ACAGUUC | 303 |
| 12327 | CAUAGAU CUGAUGAGGCCGAAAGGCCGAA ACCAAGA | 304 |
| 12330 | UAUCAUA CUGAUGAGGCCGAAAGGCCGAA AUGACCA | 305 |
| 12337 | GGUAUCA CUGAUGAGGCCGAAAGGCCGAA AGAUGAC | 306 |
| 12374 | AGUCGUG CUGAUGAGGCCGAAAGGCCGAA AACACCA | 307 |
| 12453 | ACAGUGG CUGAUGAGGCCGAAAGGCCGAA AGUCUCU | 308 |
| 12481 | GAACCGG CUGAUGAGGCCGAAAGGCCGAA ACAACAG | 309 |
| 12592 | UGCUUCA CUGAUGAGGCCGAAAGGCCGAA AAUGAGC | 310 |
| 12650 | GAUGACC CUGAUGAGGCCGAAAGGCCGAA AGAUUGA | 311 |
| 12974 | GGGCCAG CUGAUGAGGCCGAAAGGCCGAA AAUGUGG | 312 |
| 12976 | UAAGACU CUGAUGAGGCCGAAAGGCCGAA ACUUGCC | 313 |
| 13119 | GUAGAAG CUGAUGAGGCCGAAAGGCCGAA AAGGCCU | 314 |
| 13226 | AACAACC CUGAUGAGGCCGAAAGGCCGAA AGACACU | 315 |
| 13228 | AACAACC CUGAUGAGGCCGAAAGGCCGAA AGACACU | 316 |
| 13839 | UACACAA CUGAUGAGGCCGAAAGGCCGAA AAUACCA | 317 |
| 13848 | GACGGGA CUGAUGAGGCCGAAAGGCCGAA AAGCUUA | 318 |

TABLE VI

Unique Human apo(a) Hairpin Ribozyme Sequence

| nt. | Hairpin Ribozyme Sequence | SEQ ID NO. | Subutrate Sequence | SEQ ID NO. |
|---|---|---|---|---|
| 378 | GGCGCGAC AGAA GUCC ACCAGAGAAACACACGUUGUGGUACAUUACCUGGUA | 319 | GGACU GCC GUCGCGCC | 337 |
| 381 | GGAGGCGC AGAA GCAG ACCAGAGAAACACACGUUGUGGUACAUUACCUGGUA | 320 | CUGCC GUC GCGCCUCC | 338 |
| 440 | UUUGCUCA AGAA GUGC ACCAGAGAAACACACGUUGUGGUACAUUACCUGGUA | 321 | GCACC GAC UGAGCAAA | 339 |
| 7964 | UCUGCUCA AGAA GUGC ACCAGAGAAACACACGUUGUGGUACAUUACCUGGUA | 322 | GCACC GAC UGAGCAGA | 340 |
| 10215 | CAAUAAGG AGAA GCCA ACCAGAGAAACACACGUUGUGGUACAUUACCUGGUA | 323 | UGGCA GCC CCUUAUUG | 341 |
| 10534 | UGGAUUUC AGAA GUAG ACCAGAGAAACACACGUUGUGGUACAUUACCUGGUA | 324 | CUACU GCC GAAAUCCA | 342 |
| 10557 | CACCAAGG AGAA GCCA ACCAGAGAAACACACGUUGUGGUACAUUACCUGGUA | 325 | UGGCA GCC CCUUGGUG | 343 |
| 10638 | GGGACGAA AGAA GUCC ACCAGAGAAACACACGUUGUGGUACAUUACCUGGUA | 326 | GGACU GCC UUCGUCCC | 344 |
| 10700 | UUUCCUCA AGAA GUGC ACCAGAGAAACACACGUUGUGGUACAUUACCUGGUA | 327 | GCACU GAC UGAGGAAA | 345 |
| 11343 | UGUUCAGA AGAA GCCG ACCAGAGAAACACACGUUGUGGUACAUUACCUGGUA | 328 | CGGCU GUU UCUGAACA | 346 |
| 11379 | CAGUCCUG AGAA GUGG ACCAGAGAAACACACGUUGUGGUACAUUACCUGGUA | 329 | CCACA GUC CAGGACUG | 347 |

TABLE VI-continued

Unique Human apo(a) Hairpin Ribozyme Sequence

| nt. | Hairpin Ribozyme Sequence | SEQ ID NO. | Subutrate Sequence | SEQ ID NO. |
|---|---|---|---|---|
| 12342 | ACUGGAAC AGAA GUGG ACCAGAGAAACACACGUUGUGGUACAUUACCUGGUA | 330 | CCACU GUU GUUCCAGU | 348 |
| 12804 | GGCUCCUG AGAA GCCC ACCAGAGAAACACACGUUGUGGUACAUUACCUGGUA | 331 | GGGCU GCC CAGGAGCC | 349 |
| 12877 | AGGGUUAC AGAA GUAA ACCAGAGAAACACACGUUGUGGUACAUUACCUGGUA | 332 | UUACU GCC GUAACCCU | 350 |
| 13139 | GAGCAGCA AGAA GCAC ACCAGAGAAACACACGUUGUGGUACAUUACCUGGUA | 333 | GUGCU GAC UGCUGCUC | 351 |
| 13256 | GCUCCAAG AGAA GCCU ACCAGAGAAACACACGUUGUGGUACAUUACCUGGUA | 334 | AGGCU GUU CUUGGAGC | 352 |
| 13522 | ACCCUGGC AGAA GUCA ACCAGAGAAACACACGUUGUGGUACAUUACCUGGUA | 335 | UGACA GUU GCCAGGGU | 353 |
| 13794 | UAGCUGGG AGAA GUGU ACCAGAGAAACACACGUUGUGGUACAUUACCUGGUA | 336 | ACACU GUU CCCAGCUA | 354 |

TABLE VII

Unique Monkey apo(a) Hairpin Ribozyme Sequence

| nt. | Hairpin Ribozyme Sequence | SEQ ID NO. | Subutrate Sequence | SEQ ID NO. |
|---|---|---|---|---|
| 57 | GGUGCGAC AGAA GUCC ACCAGAGAAACACACGUUGUGGUACAUUACCUGGUA | 355 | GGACU GCC GUCGCACC | 374 |
| 60 | GGAGGUGC AGAA GCAG ACCAGAGAAACACACGUUGUGGUACAUUACCUGGUA | 356 | CUGCC GUC GCACCUCC | 375 |
| 119 | UUUGCUCA AGAA GUGC ACCAGAGAAACACACGUUGUGGUACAUUACCUGGUA | 357 | GCACC GAC UGAGCAAA | 376 |
| 318 | CAAUAAGG AGAA GCCA ACCAGAGAAACACACGUUGUGGUACAUUACCUGGUA | 358 | UGGCA GCC CCUUAUUG | 377 |
| 660 | CAAUAAGG AGAA GCCA ACCAGAGAAACACACGUUGUGGUACAUUACCUGGUA | 359 | UGGCA GCC CCUUAUUG | 378 |
| 744 | GGAGGUGC AGAA GCAG ACCAGAGAAACACACGUUGUGGUACAUUACCUGdUA | 360 | CUGCA GUC GCACCUCC | 379 |
| 803 | UUUGCUCA AGAA GUGC ACCAGAGAAACACACGUUGUGGUACAUUACCUGGUA | 361 | GCACC GAC UGAGCAAA | 380 |
| 1002 | CAAUAAGG AGAA GCCA ACCAGAGAAACACACGUUGUGGUACAUUACCUGGUA | 362 | UGGCA GCC CCUUAUUG | 381 |
| 1083 | GGUGCGAC AGAA GUCC ACCAGAGAAACACACGUUGUGGUACAUUACCUGGUA | 363 | GGACU GCC GUCGCACC | 382 |
| 1086 | GGAGGUGC AGAA GCAG ACCAGAGAAACACACGUUGUGGUACAUUACCUGGUA | 364 | CUGCC GUC GCACCUCC | 383 |
| 1321 | UGGAUUUC AGAA GUAG ACCAGAGAAACACACGUUGUGGUACAUUACCUGGUA | 365 | CUACU GCC GAAAUCCA | 384 |
| 1344 | CACCAAGG AGAA GCCA ACCAGAGAAACACACGUUGUGGUACAUUACCUGGUA | 366 | UGGCA GCC CCUUGGUG | 385 |
| 2130 | UGUUCAGA AGAA GCCA ACCAGAGAAACACACGUUGUGGUACAUUACCUGGUA | 367 | UGGCU GUU UCUGAACA | 386 |
| 2500 | GACCCCAG AGAA GUUU ACCAGAGAAACACACGUUGUGGUACAUUACCUdGUA | 368 | AAACA GCC CUGGGGUC | 387 |
| 3129 | ACCGGAAC AGAA GUGG ACCAGAGAAACACACGUUGUGGUACAUUACCUGGUA | 369 | CCACU GUU GUUCCGGU | 368 |
| 3683 | AAGCAGCA AGAA GCAC ACCAGAGAAACACACGUUGUGGUACAUUACCUGGUA | 370 | GUGCU GAC UGCUGCUU | 389 |
| 3890 | AAUUUGGA AGAA GCAG ACCAGAGAAACACACGUUGUGGUACAUUACCUGGUA | 371 | CUGCC GUC UCCAAAUU | 390 |
| 3912 | UCAGUCCA AGAA GUGA ACCAGAGAAACACACGUUGUGGUACAUUACCUGGUA | 372 | UCACU GCC UGGACUGA | 391 |
| 4365 | UAGCUGGG AGAA GUGU ACCAGAGAAACACACGUUGUGGUACAUUACCUGGUA | 373 | ACACU GUC CCCAGCUA | 392 |

We claim:

1. An enzymatic RNA molecule which specifically cleaves RNA encoding apo(a) RNA, wherein said enzymatic RNA molecule comprises a substrate binding site and a nucleotide sequence within or surrounding said substrate binding site wherein said nucleotide sequence imparts to said enzymatic RNA molecule activity for the cleavage of said apo(a) RNA.

2. The enzymatic RNA molecule of claim 1, wherein said substrate binding site is complementary to said apo(a) RNA.

3. The enzymatic RNA molecule of claim 1, wherein said enzymatic RNA molecule is in a hammerhead motif.

4. The enzymatic RNA molecule of claim 2, wherein said substrate binding site comprises between 12 and 100 nucleotides complementary to said apo(a) RNA.

5. The enzymatic RNA molecule of claim 2, wherein said substrate binding site comprises between 14 and 24 nucleotides complementary to said apo(a) RNA.

6. An expression vector comprising a nucleic acid sequence encoding one or more enzymatic RNA molecules of claim 1 in a manner which allows expression of said enzymatic RNA molecules.

7. The expression vector of claim 6, wherein said expression vector is a viral vector.

8. The expression vector of claim 7, wherein said viral vector is a retrovirus vector.

9. The enzymatic RNA molecule of claim 1, wherein said enzymatic RNA molecule is chemically synthesized.

10. The enzymatic RNA molecule of claim 1, wherein said enzymatic RNA molecule is in a purified form.

11. The enzymatic RNA molecule of claim 1, wherein said enzymatic RNA molecule is active in the presence of divalent metal ions.

12. The enzymatic RNA molecule of claim 11, wherein said divalent metal ion is magnesium.

13. The enzymatic RNA molecule of claim 1, wherein said enzymatic RNA molecule comprises a sugar modification.

14. The expression vector of claim 6, wherein said nucleic acid sequence encoding said enzymatic RNA molecule is under the control of a mammalian transcription promoter.

15. The expression vector of claim 6, wherein said expression vector is a plasmid DNA vector.

16. The expression vector of claim 7, wherein said viral vector is an adenovirus vector.

17. The expression vector of claim 7, wherein said viral vector is an adeno-associated virus vector.

18. The expression vector of claim 7, wherein said viral vector is an alpha virus vector.

19. The expression vector of claim 18, wherein said viral vector is a Sindbis virus vector.

20. A method of cleaving apo(a) RNA comprising the step of contacting said apo(a) RNA with the enzymatic RNA molecule of claim 1 under conditions suitable for the cleavage of said apo(a) RNA.

* * * * *